US008771689B2

(12) United States Patent
Steinman et al.

(10) Patent No.: US 8,771,689 B2
(45) Date of Patent: Jul. 8, 2014

(54) ALPHA B-CRYSTALLIN AS A THERAPY FOR ISCHEMIA OR INFLAMMATION

(75) Inventors: Lawrence Steinman, Stanford, CA (US); Shalina Sheryl Ousman, Stanford, CA (US); William H. Robinson, Palo Alto, CA (US)

(73) Assignees: The Board of Trustees of the Leland Stanford Junior University, Palo Alto, CA (US); Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/135,079

(22) Filed: Jun. 23, 2011

(65) Prior Publication Data

US 2011/0318346 A1    Dec. 29, 2011

Related U.S. Application Data

(60) Continuation-in-part of application No. 12/931,001, filed on Jan. 21, 2011, which is a division of application No. 12/001,553, filed on Dec. 11, 2007, now Pat. No. 7,875,589.

(60) Provisional application No. 60/921,211, filed on Mar. 29, 2007, provisional application No. 60/874,385, filed on Dec. 11, 2006.

(51) Int. Cl.
*A61K 39/395* (2006.01)
*A61K 38/00* (2006.01)

(52) U.S. Cl.
USPC ...................................... 424/134.1; 514/17.7

(58) Field of Classification Search
CPC .............. A61K 39/3955; A61K 45/06; A61K 2039/505; A61K 2300/00; A61K 38/00; A61K 47/48384; A61K 31/711; A61K 38/1709; C07K 2317/24; C07K 2317/92; C07K 2317/56; C07K 2317/76
USPC ..................... 424/133.1, 158.1, 178.1, 134.1; 435/375; 514/17.7, 21.2, 17.9, 17.8, 514/1.9, 16.4, 16.6; 530/387.3, 391.7, 350, 530/389.2
See application file for complete search history.

(56) References Cited

U.S. PATENT DOCUMENTS

| | | | |
|---|---|---|---|
| 6,022,859 | A | 2/2000 | Kiessling et al. |
| 6,780,971 | B2 | 8/2004 | Wolozin et al. |
| 2005/0013824 | A1 | 1/2005 | Van Noort et al. |
| 2010/0004168 | A1 | 1/2010 | Gehlbach et al. |

FOREIGN PATENT DOCUMENTS

| | | |
|---|---|---|
| EP | 0764273 | 10/1998 |
| EP | 1288226 | 3/2003 |
| WO | 95/33997 | 12/1995 |
| WO | 99/62554 | 12/1999 |
| WO | 2006/052821 | 5/2006 |

OTHER PUBLICATIONS

Peppel et al. A tumor necrosis factor (TNF) receptor-IgG heavy chain chimeric protein as a bivalent antagonist of TNF activity. J Exp Med. Dec. 1, 1991;174(6):1483-9.*
Chabas et al., "The influence of the proinflammatory cytokine, osteopontin, on autoimmune demyelinating disease," Science, 2001, 294(5547):1731-1735.
Chou et al., "CD4 T-cell epitopes of human alpha B-crystallin," J Neurosci. Res., 2004, 75(4):516-523.
Dubin et al., "Human alpha B-crystallin gene and preferential promoter function in lens," Genomics, 1990, 7 (4):594-601.
GenBank Accession No. BT006770 (2007), retrieved Jan. 25, 2008.
Sotgiu et al., "Alpha B-crystallin is not a dominant peripheral T-cell autoantigen in multiple sclerosis amongst Sardinians," Eur. J Neurol., 2003, 10(5):583-586.
Thoua et al., "Encephalitogenic and immunogenic potential of the stress protein alphaB-crystallin in Biozzi ABH (H-2A (g7)) mice," J Neuroimmunol., 2000, 104(1):47-57.
Van Stipdonk et al., "T- and B-cell nonresponsiveness to self-alphaB-crystallin in SJL mice prevents the induction of experimental allergic encephalomyelitis," Cell Immunol., 2000, 204(2):128-134.
Van Stipdonk et al., "Tolerance controls encephalitogenicity of alphaB-crystallin in the Lewis rat," J Neuroimmunol., 2000, 103(2):103-111.
Van Veen et al., "[Alpha]B-crystallin genotype has impact on the multiple sclerosis phenotype," Neurology, 2003, 61:1245-1249.
Johnson, K. P.; et al., "Extended use of glatiramer acetate (Copaxone) is well tolorated and maintains its clinical effect on multiple sclerosis relapse rate and degree of disability", Neurology, 1998, 50:701-708.
Li, David Wan-Cheng; et al., "Calcium-activated RAF/MEK/ERK Signaling Pathway Mediates p53-dependent Apoptosis and Is Abrogated by alphaB-Crystallin through Inhibition of RAS Activation", Molecular Biology of the Cell, Sep. 2005, 16:4437-4453.
Moss, Ronald B; et al., "Th1/Th2 cells in inflammatory disease states: therapeutic implications", Expert Opin. Biol. Ther., 2004, 4(12):1887-1896.
Outeiro, Tiago Fleming; et al., "Small heat shock proteins protect against alpha-synuclein-induced toxicity and aggregation", Biochemical and Biophysical Research Communications, 2006, 351:631-638.
Raman, Bakthisaran; et al., "alphaB-crystallin, a small heat-shock protein, prevents the amyloid fibril growth of an amyloid beta-peptide and beta2-microglobulin", Biochem. J., 2005, 392:573-581.

(Continued)

*Primary Examiner* — Gregory S Emch
(74) *Attorney, Agent, or Firm* — Bozicevic, Field & Francis LLP; Pamela J. Sherwood

(57) ABSTRACT

The invention provides methods for treating inflammatory diseases by administering to the subject an effective amount of an agent that provides alpha B-crystallin activity, where the dose is effective to suppress or prevent initiation, progression, or relapses of disease, including the progression of established disease. In some embodiments, the methods of the invention comprise administering to a subject having a pre-existing inflammatory disease condition, an effective amount of alpha B-crystallin protein, to suppress or prevent relapses of the disease.

7 Claims, 24 Drawing Sheets
(11 of 24 Drawing Sheet(s) Filed in Color)

(56) References Cited

OTHER PUBLICATIONS

Solomon, Beka; et al., "Monoclonal antibodies inhibit in vitro fibrillar aggregation of the Alzheimer beta-amyloid peptide", PNAS, Jan. 1996, 93:452-455.

Wang, Jiou; et al., "Somatodendritic accumulation of misfolded SOD1-L126Z in motor neurons mediates degeneration: alphaB-crystallin modulates aggregation", Human Molecular Genetics, 2005, 14(16):2335-2347.

Lo et al. (1998. Protein Engineering 11:495-500).

Rekas 2004 (Journal of Molecular Biology 340:1167-1183).

Nagaraj; et al.. "Oicarbonyl stress and apoptosis of vascular cells—Prevention by alpha B-crystallin", Annals of the New York Academy of Sciences (2005), pp. 158-165.

Roelofs; et al., "Identification of small heat shock protein B8 (HSP22) as a novel TLR4 ligand and potential involvement in the pathogenesis of rheumatoid arthritis", Journal of Immunology (2006), 176(11):7021-7027.

* cited by examiner

ALPHA B-CRYSTALLIN AS A THERAPY FOR ISCHEMIA OR INFLAMMATION

BACKGROUND OF THE INVENTION

Alpha B-crystallin (αBC) is a member of the small heat shock family of proteins that is found in high levels in the ocular lens. Along with alpha A, beta and γ-crystallin, αBC forms the major water soluble structural protein of the vertebrate ocular lens that produces the necessary refractive index. Alpha crystallins are also implicated as molecular chaperones where they are proposed to bind unfolded and denatured proteins thereby suppressing non-specific aggregation and maintaining lens transparency. Interestingly, mice null for αBC have normal lenses indicating that this crystallin is not essential for development of the transparent lens. In addition to the lens of the eyes, high levels of αBC are found in the adult heart and skeletal muscle, with lower expression in kidney, lung, CNS glia, liver and developing heart and somites.

αBC expression is associated with a number of pathological conditions. Increased levels of αBC are found in oncogenic malignancies and in CNS glia of various neurological diseases such as Alexander's disease, Creutzfeldt-Jacob disease, Alzheimer's disease, Parkinson's disease, Multiple Sclerosis, and neurotropic infections. Heat shock and transition metals can also induce the expression of this crystallin in primary astrocytes.

Multiple Sclerosis (MS) is an autoimmune disease of the CNS of unknown etiology that affects ~400 000 Americans. In MS, myelin reactive T cells enter into the brain and spinal cord and mediate destruction of the myelin sheath surrounding neurons resulting in progressive motor dysfunction and eventual paralysis. Current treatment strategies include switching the pro-inflammatory Th1 and Th17 T cell phenotype to an anti-inflammatory Th2 response, preventing encephalitogenic T cells from extravasating into the brain, inducing T cell tolerance, anergy or apoptosis, and repairing or replacing damaged CNS cells, such as neurons and oligodendrocytes.

The course of disease is highly varied and unpredictable. In most patients, especially when MS begins with optic neuritis, remissions can last months to >10 yr. However, some patients have frequent attacks and are rapidly incapacitated, although life span is shortened only in very severe cases.

Goals for therapy include shortening acute exacerbations, decreasing frequency of exacerbations, and relieving symptoms; maintaining the patient's ability to walk is particularly important. Acute exacerbations may be treated with brief courses of corticosteroids. However, although they may shorten acute attacks and perhaps slow progression, corticosteroids have not been shown to affect long-term outcome.

Immunomodulatory therapy decreases frequency of acute exacerbations and delays eventual disability. Immunomodulatory drugs include interferons (IFNs), such as IFN-β1b and IFN-β1a. Glatiramer acetate may also be used. Other potential therapies include the immunosuppressant methotrexate and Natalizumab, an anti-α$_4$ integrin antibody that inhibits passage of leukocytes across the blood-brain barrier. Immunosuppressants such as mycophenolate and cyclophosphamide have been used for more severe, progressive MS but are controversial.

In addition to suppressing the pathological immune response it is important to protect CNS cells from further damage and to induce repair of injured cells since some cells such as neurons have few progenitors in the adult mammalian brain and are thus limiting.

Early studies in MS patients implied that αBC may have an autoantigenic role in this disease. Myelin isolated from MS brains contained a single fraction that turned out to be αBC that was localized to oligodendrocytes and astrocytes and proved highly immunodominant to MS and control T cells by inducing proliferation and IFN-γ production. In large scale transcriptional profiling of MS brain lesions with a robot capable of sequencing genes Chabas et. al. (2001) Science 294, 1731-5 also found αBC to be the most abundant gene transcribed in early active MS. Three polymorphisms at positions C249G, C650G and A652G in the αBC gene have also been found to be associated with susceptibility to MS and disease expression (van Veen et al. (2003) Neurology 61, 1245-9). Further evidence for an autoantigenic role of αBC in MS include increased proliferation of, and production of IL-2, IFN-y and TNF from CD4+ T cell lines in response to αBC peptides from early active MS patients (Chou et al. (2004) J Neurosci Res 75, 516-23). It has been suggested that the protein is taken up for class II MHC-restricted presentation to T cells by local APC is these lesions.

The role of αBC in EAE and MS is discussed in, for example, van Stipdonk et al. (2000) J Neuroimmunol 103, 103-11; van Stipdonk et al. (2000) Cell Immunol 204, 128-34; Thoua et al. (2000) J Neuroimmunol 104, 47-57; and Sotgiu et al. (2003) Eur J Neurol 10, 583-6 (2003).

SUMMARY OF THE INVENTION

The invention provides methods for treating inflammatory or ischemic diseases, including neurological inflammatory diseases, which may be demyelinating autoimmune diseases, such as multiple sclerosis, neuromyelitis optica, chronic inflammatory demyelinating polyneuropathy, etc. and the like. In other embodiments, inflammatory diseases include, without limitation, rheumatoid arthritis, atherosclerosis, stroke, myocardial infarction and peripheral arterial vascular disease, Alzheimer's disease, Parkinson's disease and amyotrophic lateral sclerosis, also known as Lou Gehrig's disease. The methods of the invention comprise administering to the subject an effective amount of an agent that provides alpha B-crystallin activity, where the dose is effective to suppress or prevent initiation, progression, or relapses of disease, usually prevention of the progression of disease or sequelae following an acute incident. The administration may be systemic, including intravenous, intramuscular, intraperitoneal, subcutaneous, etc., and usually other than oral administration. In some embodiments, the methods of the invention comprise administering to a subject having a pre-existing inflammatory disease condition, an effective amount of alpha B-crystallin protein, to suppress or prevent relapses of the disease.

The mitogen activated protein kinases are key players in inflammation and have been shown to play a key role in the pathogenesis of myocardial infarction, stroke, and peripheral arterial ischemia, Alzheimer's Disease, Parkinson's Disease and Amyotrophic Lateral Sclerosis. The absence of aBC influences the p38 MapK and ERK pathways in brain and in peripheral macrophages and lymphocytes. By influencing these pathways in the central nervous system, administration of aBC affects inflammatory neurological diseases, such as multiple sclerosis, neuromyelitis optica, Alzheimer's Disease, Parkinson's Disease, amyotrophic lateral sclerosis and stroke. Administration of aBC diminishes the extent and severity of ischemic lesions, including myocardial infarction, stroke and arterial occlusion.

In some embodiments, a method is provided for inhibiting disease in a subject, the method comprising administering to the subject a prophylactically effective amount of a nucleic acid that specifically enhances levels of alpha B-crystallin, e.g. by providing a nucleic acid that encodes alpha B-crystallin operably linked to a promoter. In other embodiments, a method is provided for inhibiting disease in a subject, the method comprising administering to the subject a therapeutically effective amount of alpha B-crystallin polypeptide, e.g. a recombinantly produced polypeptide. The therapeutic agent may be administered systemically, e.g. i.v., or locally, e.g. to the site of inflammatory or ischemic lesions.

In some methods of the invention, the subject is a human. In some methods, the level of alpha B-crystallin is monitored in a cell of the patient selected from the group consisting of a T cell, a neuron, a macrophage, a vascular endothelial cell, an astrocyte and a microglial cell during therapy. In some methods, the patient has ongoing inflammatory disease and the method further comprises monitoring a decrease in the symptoms of the patient responsive to the administering of alpha B-crystallin.

In some embodiments of the invention, myelin-reactive or other activated T cells, e.g. T cells present in CSF of MS patients, or T cells present in synovial fluid of RA patients, are monitored for one or more of cytokine expression, e.g. IL-2, IFN-γ and/or IL-17; and upregulation or phosphorylation of p38MAPK and ERK, to determine, for example, if the treatment is effective in reducing the activation of such T cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Paraffin-embedded spinal cord sections taken at day 14 from WT (A, B) and $\alpha BC^{-/-}$ (C, D) animals with EAE and immuno-stained for cleaved (B, D) and uncleaved caspase-3 (A, C). 20×magnification.

Figure 9:
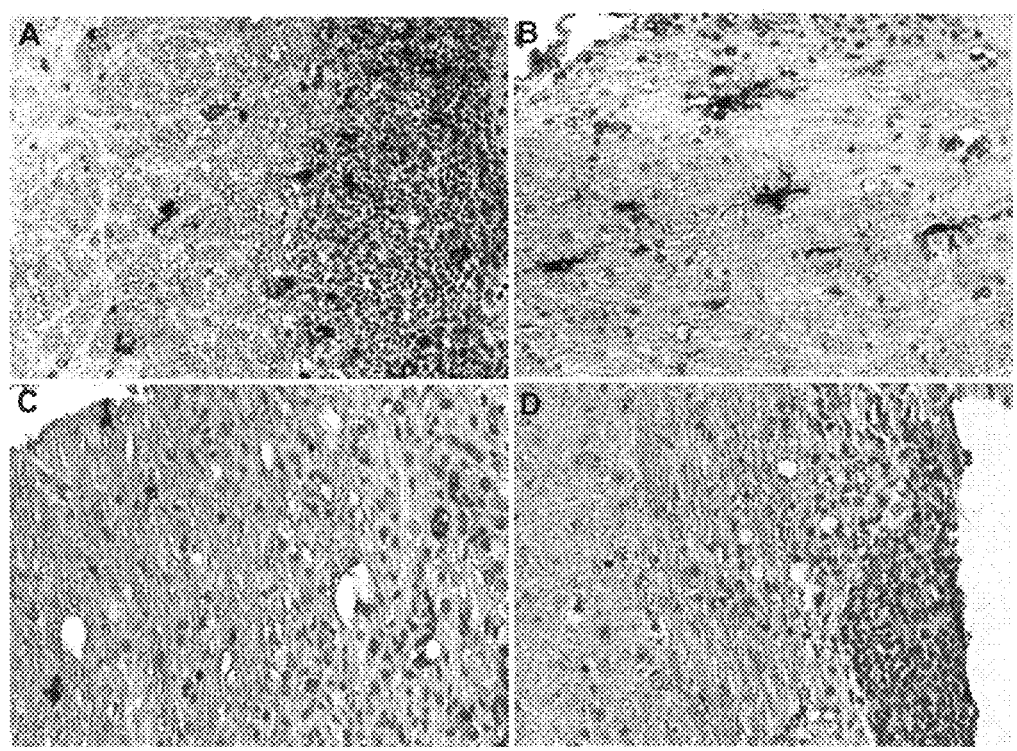

FIG. 9: EAE mice treated with αBC have fewer TUNEL positive cells in their spinal cord. Paraffin-embedded spinal cord sections taken at day 32 from WT mice with EAE and treated with PBS (A, B) and recombinant αBC (C, D) and processed for TUNEL staining. 160×magnification.

Figure 10:
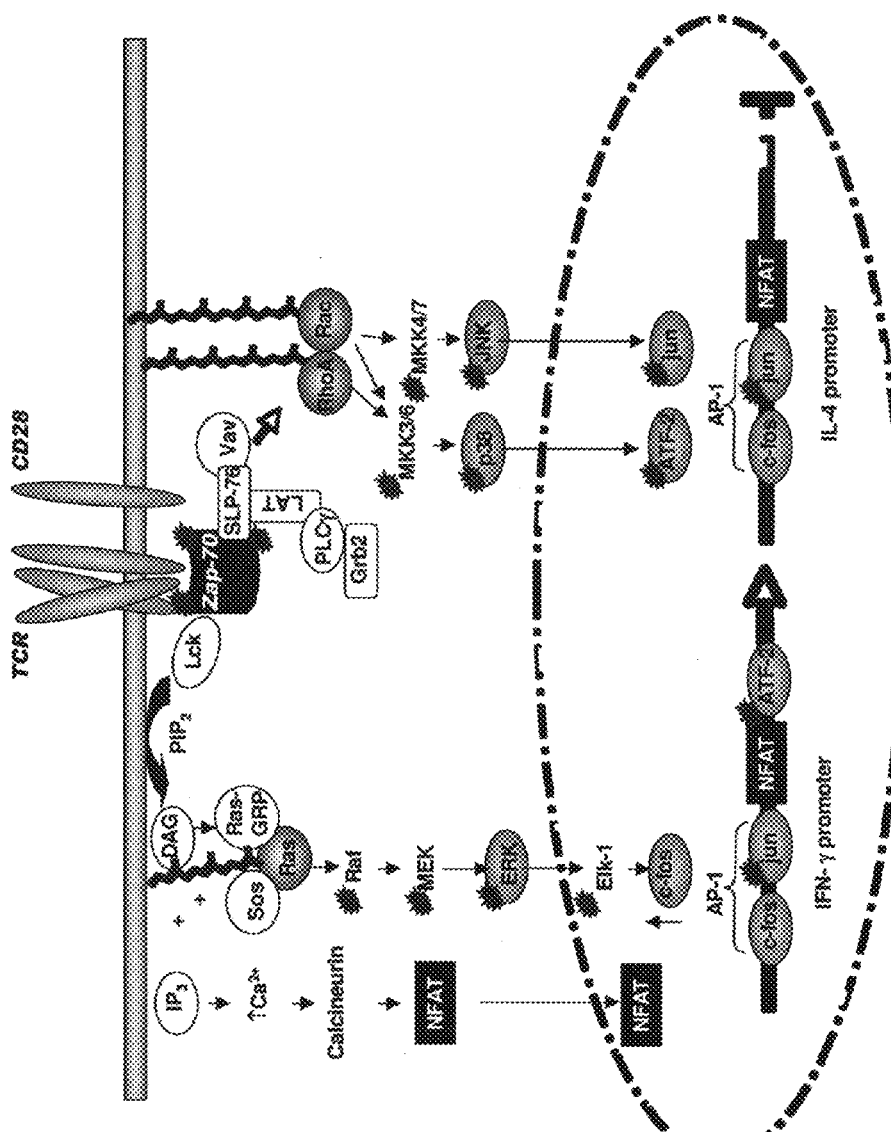

FIG. 10. Schematic of pathways involved in inflammation.

Figure 11:
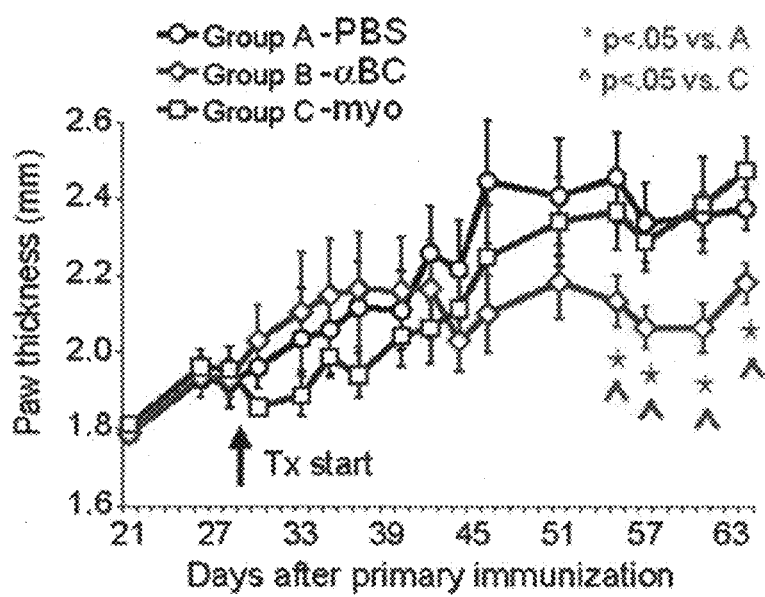

FIG. 11. αB crystallin treats established autoimmune arthritis in the collagen-induced arthritis model. DBA/1 mice were induced for collagen-induced arthritis (CIA) with bovine type II collagen emulsified in complete Freund's adjuvant, and boosted 21 days later with bovine type II collagen in incomplete Freund's adjuvant. After mice developed clinical arthritis (average paw thickness approximately 1.95 mm), arthritic mice were randomized to receive every-other day treatment with αBC (10 μg recombinant human αBC (US Biological, Swampscott, Mass.; diluted in saline), myoglobin control protein (10 μg) or PBS (saline control). Mice with established arthritis treated with αBC demonstrated statistically reduced arthritis severity relative to mice treated with the myoglobin or PBS controls (P<0.05).

Figure 12:
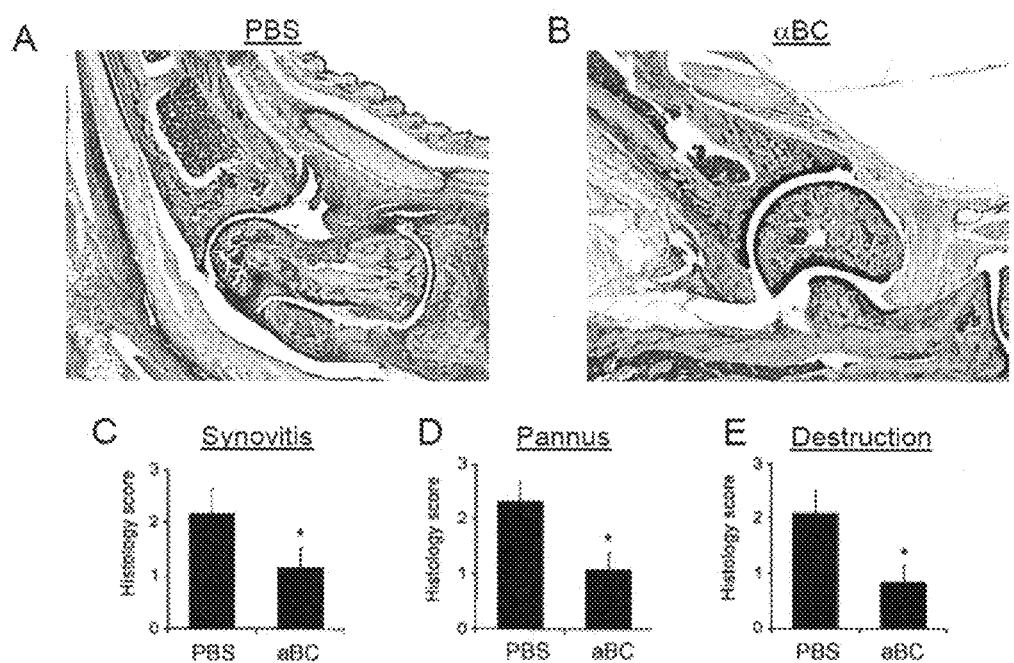

FIG. 12. αBC treatment reduces synovitis, pannus and destruction in established CIA. Mice with established CIA were treated with αBC or PBS, and following the treatment course mice were sacrificed and hind paws harvested for blinded histologic analysis. The blinded scorer assessed the hind joint sections for the degree of synovitis (inflammation), pannus (synovial lining growth) and destruction (bony erosions). CIA mice treated with αBC exhibited statistical reductions in the synovitis, pannus and destruction scores (p<0.05) further demonstrating the efficacy of αBC therapy.

Figure 13:
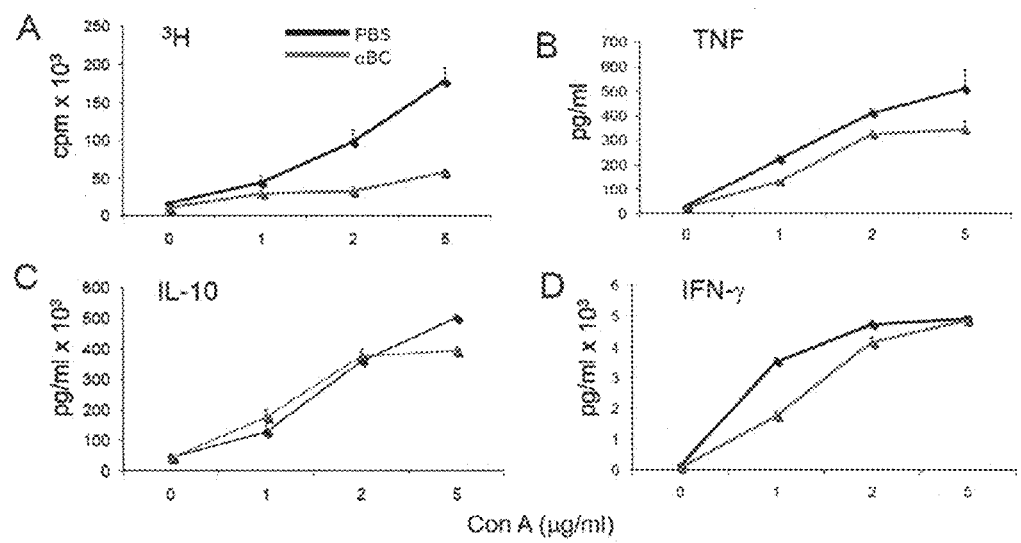

FIG. 13. Proliferation and proinflammatory cytokines are reduced in splenocytes derived from αBC-treated mice with CIA. DBA/1 mice were induced for collagen-induced arthritis (CIA) with bovine type II collagen emulsified in complete Freund's adjuvant, and boosted 21 days later with bovine type II collagen in incomplete Freund's adjuvant. After mice developed clinical arthritis, treatment with either recombinant αBC or control treatment with PBS was initiated, and 2 weeks later upon sacrifice splenocytes were harvested and stimulated with Con A (dose on X axis). Proliferative responses were measured by 3H-thymidine incorporation (A). TNF (B), IL-10 (C) and IFN-gamma (D) production was measured by ELISA. In vivo treatment of mice with CIA with aBC reduced the proliferative response (A) and pro-inflammatory cytokine production (B, D) of splenocytes.

Figure 14:
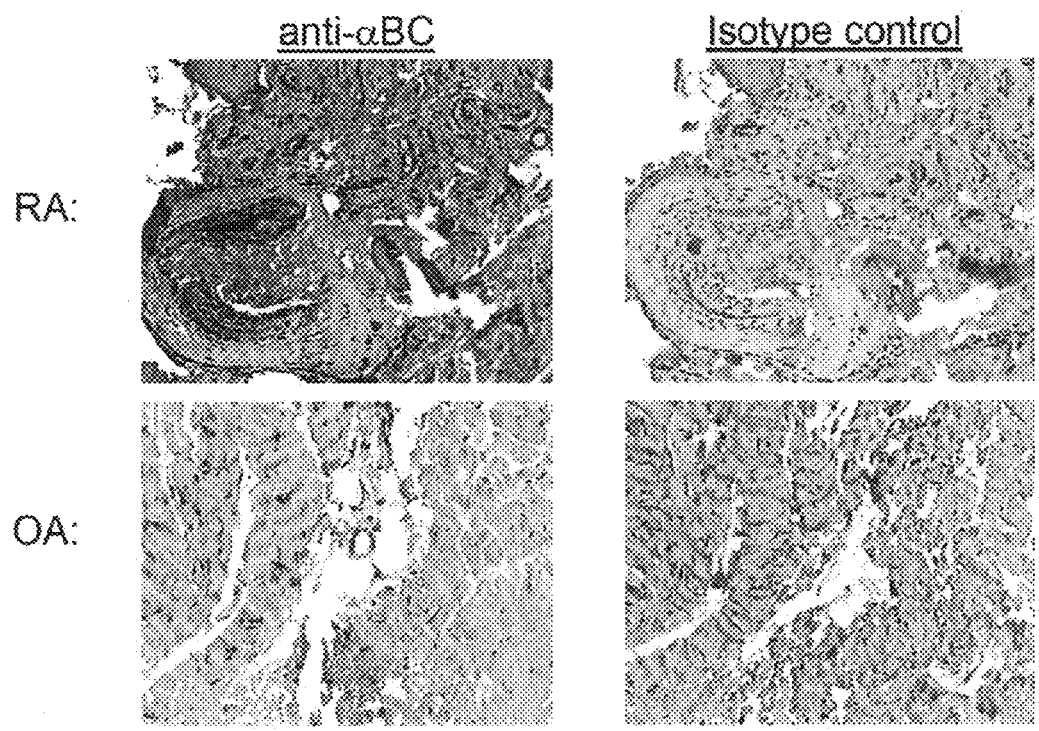

FIG. 14. aBC is expressed at high levels in RA synovial tissue. Remnant synovial lining tissue was obtained from an RA and an OA patient at the time of arthroplasty after informed consent and under human subjects protocols approved at Stanford University. The synovial lining tissue was fixed, paraffin-embedded, and sections. Immunohistochemical analysis of sections with antibodies specific for aBC as well as an isotype-matched control antibody demonstrated high levels of aBC protein expression in RA synovium but not OA synovium.

Figure 15:
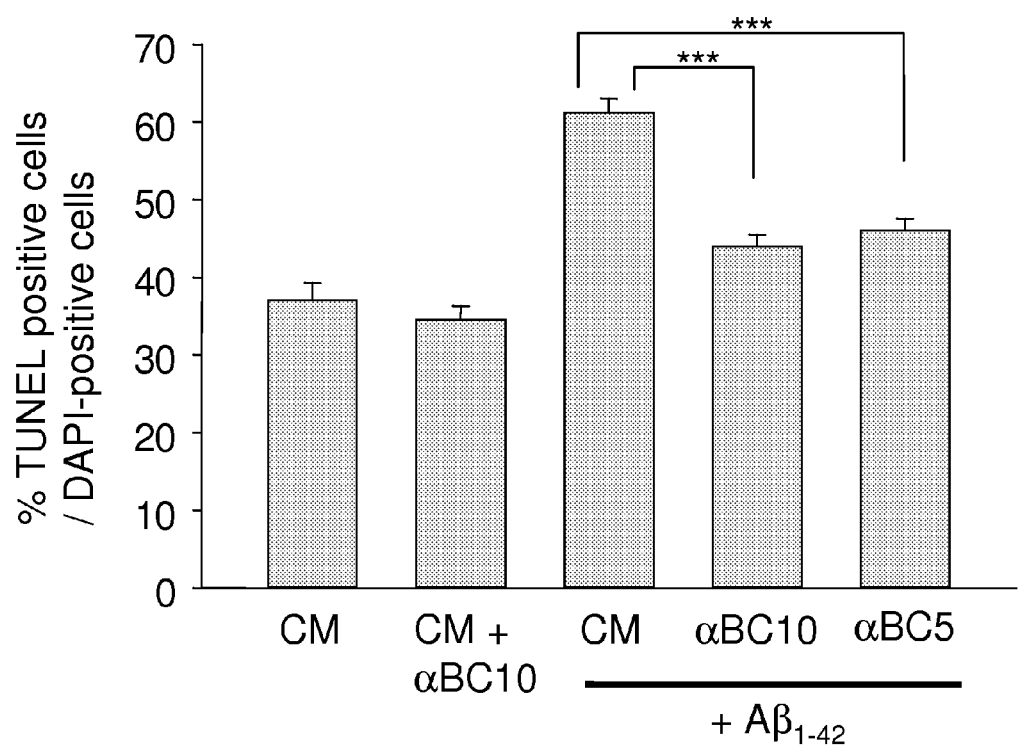

FIG. 15. αBC protects hippocampal neurons from Abeta-induced apoptosis.

Figure 16:
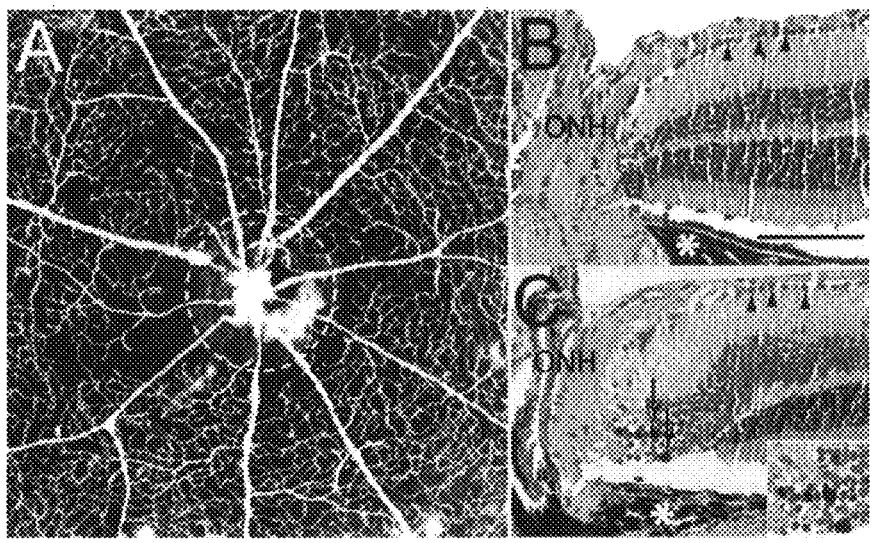

FIG. 16. Mouse experimental AION. (A) Whole mount retina following India ink angiography demonstrating the loss of microvasculature, swelling, and leakage at the optic nerve head (dashed circle) one day following optic nerve head ischemia. Horizontal H&E-stained 10 m sections of control (B) and AION (C) eyes showing the loss of retinal ganglion cells (arrowheads) and pigment laden macrophages (arrows and inset) 6 weeks following optic nerve head ischemia. ONH: optic nerve head, *: retinal pigment epithelium. Scale bar: 0.1 mm. 152×127 mm (300×300 DPI)

Figure 17:
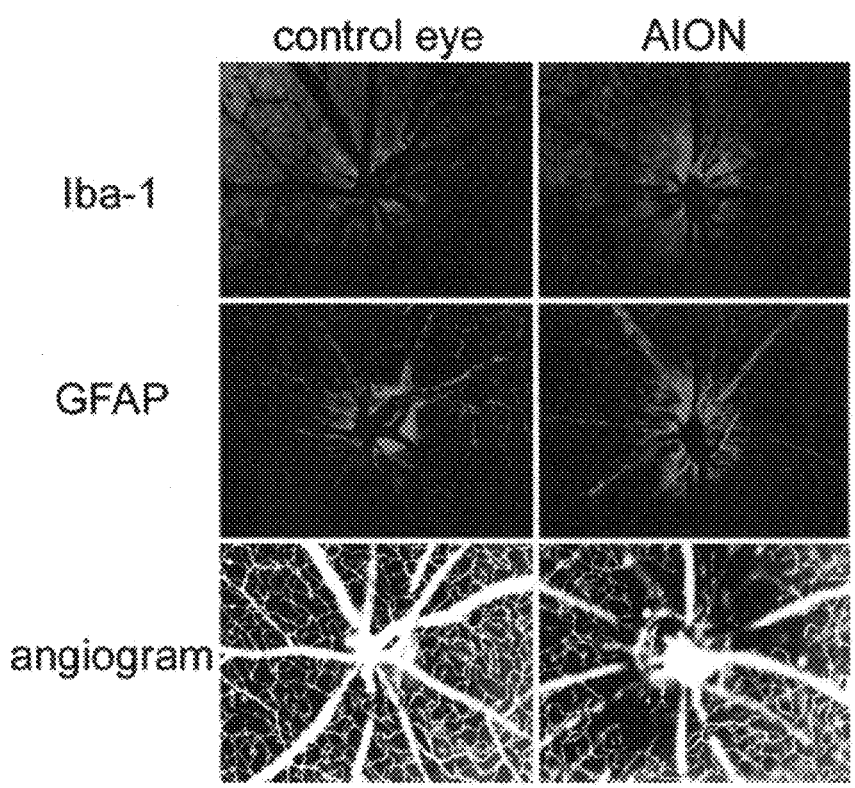

FIG. 17. Up-regulation of micro- and macroglia at the optic nerve head 3 days after experimental AION in the right eye. These whole mount neuroretina were representative specimen from one pair of eyes, stained with antibody against Iba-1 and GFAP, and perfused with India ink retinal angiography. Increased expression of Iba-1 and GFAP was limited to areas of microvascular loss. n=5 pairs of eyes. 165×152 mm (300×300 DPI)

Figure 18:
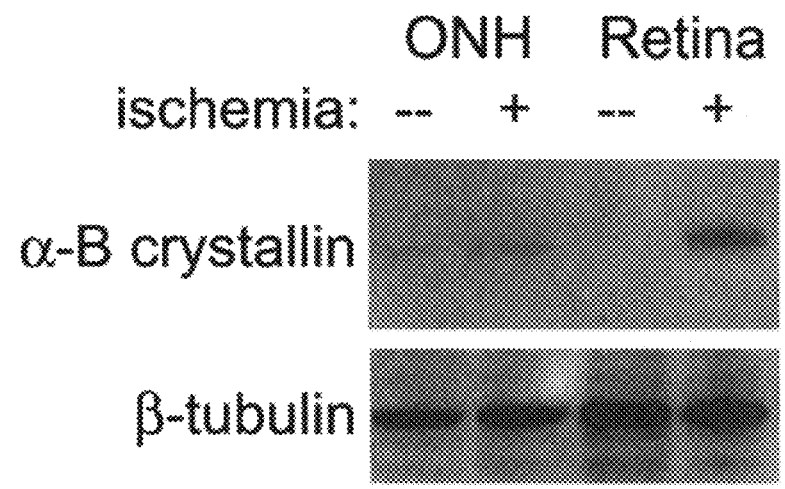

FIG. 18. Western blot showed increased expression of αBC protein (top) at the optic nerve head (ONH) and retina one day following optic nerve head ischemia. Antibody against β tubulin (bottom), a marker of retinal ganglion cell body and axons, showed equal loading of protein in the control and AION lanes. This blot was an examplar from repeated experiments, with each lane containing 2.2 g of protein prepared from the optic nerve head or neuroretina of 3 adult mice. 152×101 mm (300×300 DPI)

Figure 19:
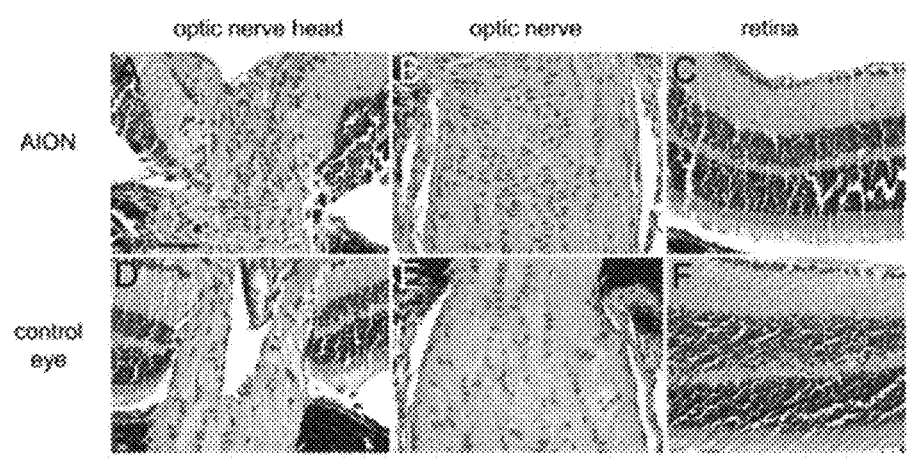

FIG. 19. Prominent post-ischemic inflammation in the optic nerve head and optic nerve of αBC knock-out mice 3 weeks after experimental AION. These are representative 10 m H&E horizontal sections from AION (top) and control (bottom) eyes, comparing the optic nerve head (A, D), optic nerve (B, E), and retina (C, F). Scale bar: 0.05 mm. n=3 pairs of eyes. 254×190mm (300×300 DPI)

Figure 20:
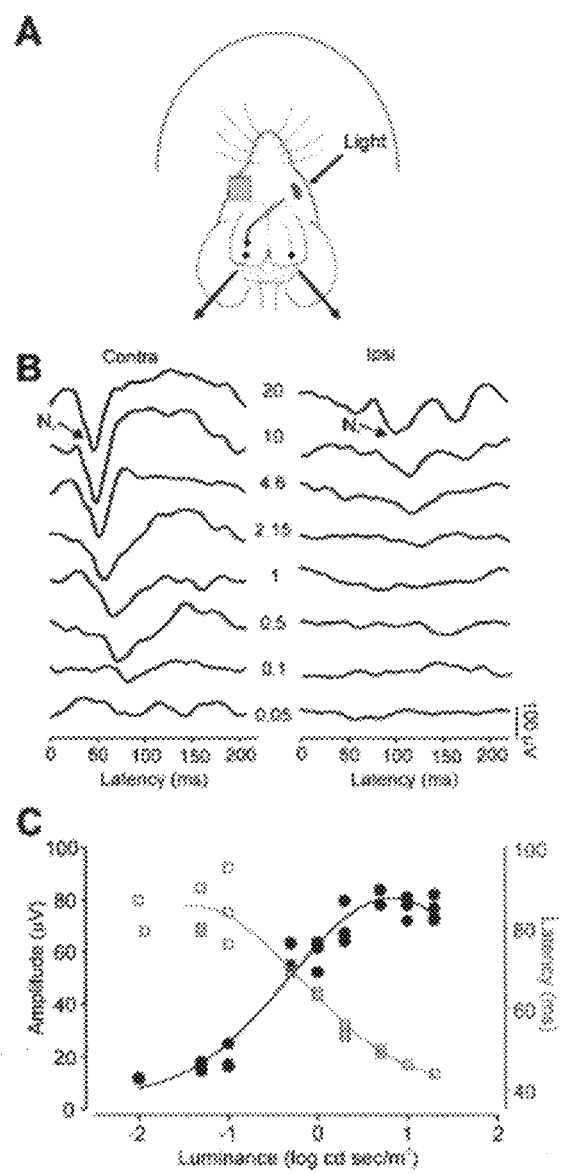

FIG. 20. Intracranial flash visual evoked potential (fVEP) recording in the mouse. (A) Schematic diagram of the recording set-up in the Ganzfeld dome. Light was presented to the right eye with the left eye occluded. Intracranial electrodes (black dots) were implanted bilaterally in the occipital lobe to assess contra- and ipsilateral cortical responses. (B) Robust contralateral photopic fVEP responses (dominant waveform $N_1$) were consistent with a predominant crossed visual pathway in rodents. Luminance intensities used (in cd sec/m$^2$) are indicated in the middle. An examplar of relatively large fVEP amplitude was chosen to illustrate responses over a large range of luminance intensities. (C) In response to increasing stimulus luminance intensities (plotted in log scale), fVEP increased in amplitude (left-sided y-axis, black circles) and decreased in the latency (right sided y axis, gray open squares).

Figure 21:
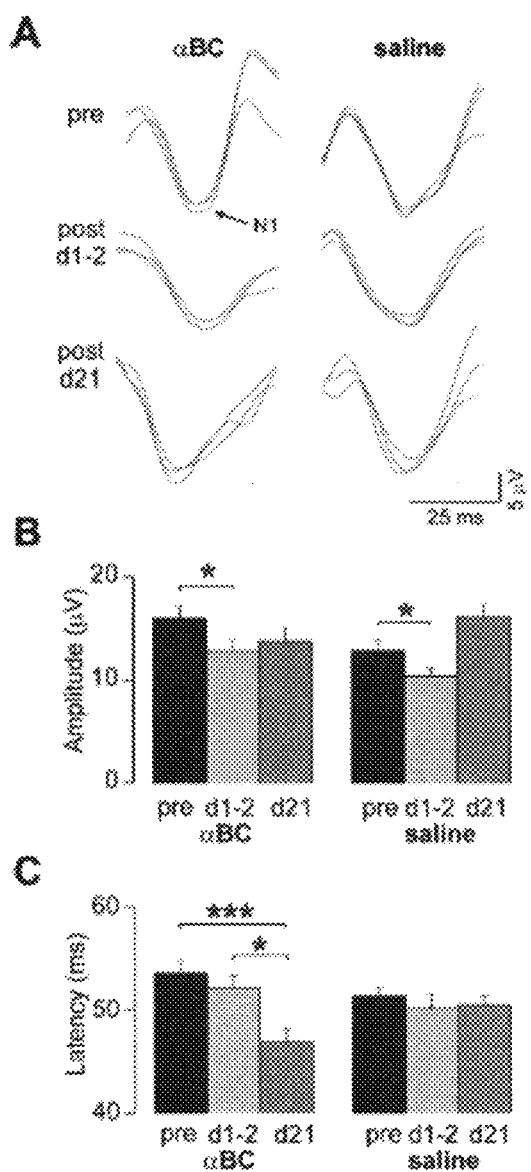

FIG. 21. Intracranial fVEP responses during αBC vs. saline treatment in experimental AION. (A) Representative fVEP traces ($N_1$) from the BC- vs. saline-treated groups at 20 cd sec/m$^e$at baseline (pre), immediately post (d1-2), and 3 weeks (d21) following optic nerve head ischemia. (B) Population data of $N_1$ peak amplitude and (C) latency in the experiment described in (A). There was a decrease in the fVEP amplitude immediately after experimental AION induction (d1-2) within each group (*$p<0.05$), which improved over time but only significantly in the saline-treated group. While there was no significant change of latency at days 1-2 within each group, latency in the αBC-treated animals improved dramatically by day 21. *$p<0.05$, days 1-2 vs. day 21. ***$p<0.0005$, baseline vs. day 21. Error bars are S.E.M.

Figure 22:
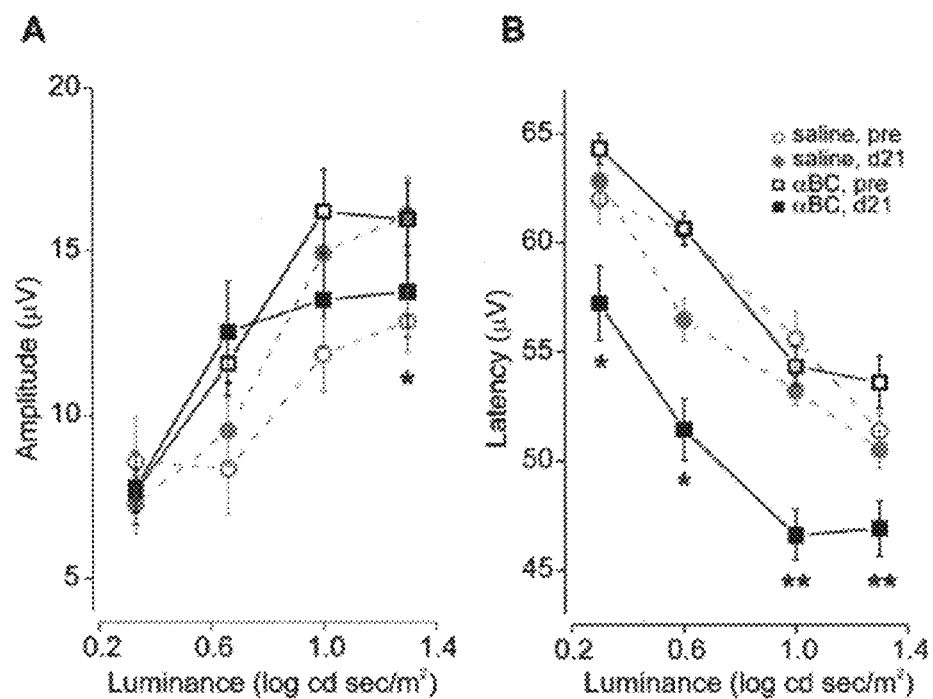

FIG. 22. Intensity series of fVEP amplitude and latency at baseline vs. day 21. (A) Amplitude increased in response to brighter luminance intensities. This pattern was similiar in the saline- and αBC-treated groups at baseline and at day 21. At day 21, *$p<0.05$, saline- vs. αBC-treated group at 20 cd sec/m$_2$. Notice the greater variability of the amplitude data compared to the latency values. (B) Latency decreased in response to brighter luminance intensities in all groups. However, after 3 weeks of αBC treatment, there was a striking acceleration of the peak fVEP responses across all luminance intensities. *$p<0.05$, saline- vs. αBC-treated group at 2.15 and 4.6 cd sec/m$_2$. **$p<0.01$ at 10 and 20 cd sec/m2.

Figure 23:
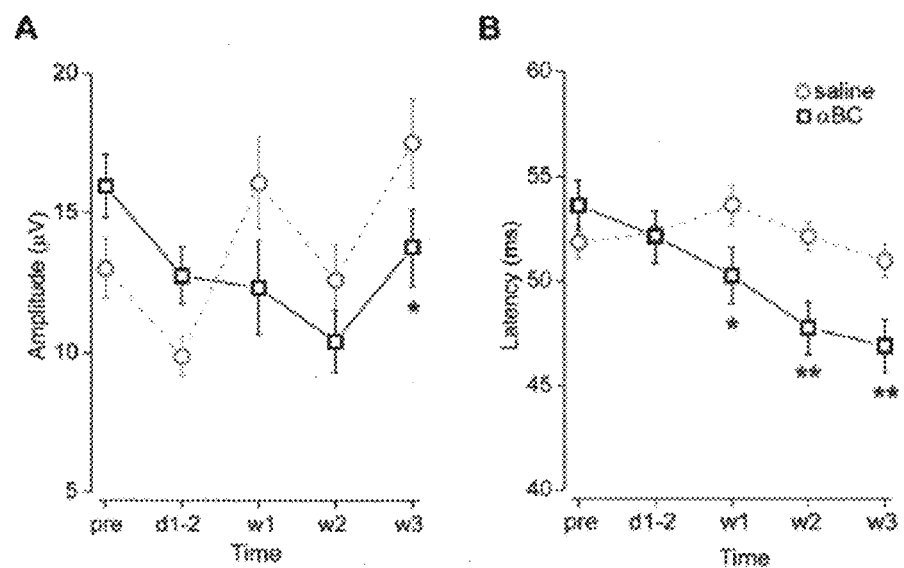

FIG. 23. Flash VEP responses to 20 cd sec/m$_2$ during 3 weeks of treatment. (A) Amplitude. Comparing αBC- vs. saline-treated groups, the amplitudes were not significantly different in all time points except for day 21 (*$p<0.05$). Notice the variability of the amplitude data compared to that of the latency. (B) Latency. By week 2 of αBC treatment, there was a significant latency improvement in the αBC-treated group, which increased further at week 3. *$p<0.05$, **$p<0.01$. Error bars are S.E.M. pre: baseline, d1-2: days 1-2, w: week.

DETAILED DESCRIPTION

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed—herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

"Activity" of alpha B-crystallin shall mean any enzymatic or binding function performed by that protein.

"Comparable cell" shall mean a cell whose type is identical to that of another cell to which it is compared. Examples of comparable cells are cells from the same cell line.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may refer to a relapse in a patient that has ongoing relapsing remitting disease. The methods of the invention are specifically applied to patients that have been diagnosed with an autoimmune disease. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Alpha B-crystallin" shall mean the human protein encoded by the mRNA sequence set forth in GenBank Accession No. BT006770 and as described by Dubin et al. (1990) Genomics 7:594-601, all naturally occurring variants and homologues thereof, and where applicable herein, all antigenic fragments thereof. The crystallins compose approximately 90% of the soluble protein of the vertebrate eye lens and include 3 major families of ubiquitously expressed crystallins: alpha, beta, and gamma. Alpha-B-crystallin is a member of the small heat-shock protein family. The human CRYAB gene which encodes a 175-amino acid protein with a molecular mass of 20 kD. The alpha-crystallin subunits alpha-A and alpha-B each can form an oligomer by itself or with the other. Interactions have also been reported between alpha-A- (or alpha-B-) and beta-B2- or gamma-C--crystallins, but the intensity of interaction was much less than that of alpha-A-alpha-B interactions. Experiments with N- and C-terminal domain-truncated mutants demonstrated that both N- and C-terminal domains were important in alpha-A-crystallin self-interaction, but that primarily the C-terminal domain was important in alpha-B-crystallin self-interaction.

Active fragments of alpha B-crystallin share a functional or binding property with full length Alpha B-crystallin.

Epitopic fragments of alpha B-crystallin bind to a monoclonal antibody that binds to full length Alpha B-crystallin.

"Alpha B-crystallin-related disorder" shall mean any disorder in which expression of alpha B-crystallin contributes to the pathogenesis.

Over-expression of alpha B-crystallin means an expression level that is greater than the mean plus one standard deviation of that in a population of normal individuals. Preferably the expression level is at least ten times the mean of that in a population of normal individuals.

"Specifically hybridize" to a nucleic acid shall mean, with respect to a first nucleic acid, that the first nucleic acid hybridizes to a second nucleic acid with greater afinity than to any other nucleic acid.

"Specifically inhibit" the expression of a protein shall mean to inhibit that protein's expression (a) more than the expression of any other protein, or (b) more than the expression of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response, which may include a component that is directed against alpha B-crystallin. An "immunogen" is capable of inducing an immunological response against itself on administration to a mammal or due to autoimmune disease.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy. eds., Academic Press 1995); Immunology Methods Manual (I.

Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of preexisting conditions. For example, the prevention of autoimmune disease may be accomplished by administration of the agent prior to development of a relapse. The treatment of ongoing disease, where the treatment stabilizes or improves the clinical symptoms of the patient, is of particular interest.

The invention provides methods for treating inflammatory diseases. Inflammatory diseases of interest include neurological inflammatory conditions, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. The methods of the invention comprise administering to the subject an effective amount of an agent that provides alpha B-crystallin activity, to suppress or prevent initiation, progression, or relapses of disease. Administration of αBC diminishes the extent and severity of ischemic lesions, including myocardial infarction, stroke and arterial occlusion.

As shown herein, alpha B crystallin provides multiple functions that act in the treatment of inflammatory conditions by suppression of pro-inflammatory cytokine production. Neurologic benefits are also obtained, including protection of CNS cells from further damage; induction of repair of CNS cells, e.g. when neurons and glial precursor cells are targeted for injury and death; suppression of T cell and macrophage proliferation.

In some methods of treatment, an αBC coding sequence is introduced into a cell to upregulate expression of αBC, where the cell may be an immune cell, a nervous system cell, etc. Alternatively, autoimmune disease in a subject is treated by administering to the subject a therapeutically effective amount of an alpha B-crystallin polypeptide, or active fragment or derivative thereof.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Conditions for Anaylsis and Therapy

The compositions and methods of the invention find use in combination with a variety of inflammatory conditions, including neurological inflammatory conditions, relapsing autoimmune conditions, and relapsing neurological inflammatory conditions.

lmmunohistochemical and molecular biological evidence has shown that the brain is capable of sustaining an immune response and that the result may be damaging to host cells. The brain, rather than being immunologically privileged, may be particularly vulnerable since neurons are postmitotic. They cannot divide so that, once lost, they are not replaced. The evidence for a chronic inflammatory reaction in the brain is particularly strong in Alzheimer's disease (AD), where it has been extensively studied, but there is also evidence that a local immune reaction occurs in affected regions of the brain in Parkinson's disease (PD) and in ALS; as well as the autoimmune neurologic diseases, e.g. MS, EAE, etc. These reactions may involve inflammatory components by local neurons and glia, and especially resident phagocytes—which, in the brain, are the microglia. The complement system, microglia, and inflammatory cytokines appear to play key roles.

Inflammatory neurological diseases include Multiple sclerosis (MS), which is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, per year. Over 10 to 20 years, approximately 50% of RR MS patients develop secondary progressive MS (SP MS) which is characterized by incomplete recovery between attacks and accumulation of neurologic deficits resulting in increasing disability.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, may show plaques. It may also detect treatable nondemyelinating lesions at the junction of the spinal cord and medulla (eg, subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions may also be visible on contrast-enhanced CT scans; sensitivity may be increased by giving twice the iodine dose and delaying scanning (double-dose delayed CT scan).

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Peripheral neuropathies include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Neuromyelitis optica (NMO), or Devic's disease, is an autoimmune, inflammatory disorder of the optic nerves and spinal cord. Although inflammation can affect the brain, the disorder is distinct from multiple sclerosis, having a different pattern of response to therapy, possibly a different pattern of autoantigens and involvement of different lymphocyte subsets.

The main symptoms of Devic's disease are loss of vision and spinal cord function. As for other etiologies of optic neuritis, the visual impairment usually manifests as decreased visual acuity, although visual field defects, or loss of color vision can occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelinization), but they differ from MS pattern II lesions in their prominent perivascular distribution. Therefore, the pattern of inflammation is often quite distinct from that seen in MS.

Attacks are conventionally treated with short courses of high dosage intravenous corticosteroids such as methylprednisolone IV. When attacks progress or do not respond to corticosteroid treatment, plasmapheresis can be used. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study.

The disease can be monophasic, i.e. a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike MS, Devic's disease rarely has a secondary progressive phase in which patients have increasing neurologic decline between attacks without remission. Instead, disabilities arise from the acute attacks.

Parkinson's disease is an idiopathic, slowly progressive, degenerative CNS disorder characterized by slow and decreased movement, muscular rigidity, resting tremor, and postural instability. Diagnosis is clinical. Treatment is with levodopa plus carbidopa, other drugs, and, for refractory symptoms, surgery. In Parkinson's disease, pigmented neurons of the substantia nigra, locus ceruleus, and other brain stem dopaminergic cell groups are lost. Loss of substantia nigra neurons, which project into the caudate nucleus and putamen, depletes dopamine in these areas.

The presence of complement proteins, including all components of the membrane attack complex, has been shown intracellularly on Lewy bodies and on oligodendroglia in the substantia nigra in PD and familial PD. Such oligodendroglia have been described as complement activated oligodendroglia.

A profusion of reactive microglia is seen in the substantia nigra and striatum, not only in idiopathic PD, but also in familial PD, as well as in the parkinsonism-dementia complex of Guam. Reactive microglia are also seen in the basal ganglia in 6-hydroxydopamine and MPTP animal models of PD, and there are several reports that anti-inflammatories inhibit dopaminergic neurotoxicity in such animal models. Microglia can be activated by products of the classical complement cascade, by various inflammatory cytokines, and by chromogranin A, which has been reported to occur in PD substantia nigra.

Increased levels of interleukin-1β, interleukin-6, and TNFα have been found in the basal ganglia and CSF of PD patients. The presence of glial cells immunoreactive for TNFα and/or interleukin-1β has also been reported in the substantia nigra of PD patients.

Alzheimer's disease causes progressive cognitive deterioration and is characterized by senile plaques, β-amyloid deposits, and neurofibrillary tangles in the cerebral cortex and subcortical gray matter. Most cases are sporadic, with late onset (>60 yr) and unclear etiology. However, about 5 to 15% are familial; ½ of these cases have an early onset (<60 yr) and are typically related to specific genetic mutations. Typically, extracellular β-amyloid deposits, intracellular neurofibrillary tangles (paired helical filaments), and senile plaques develop, and neurons are lost. Cerebrocortical atrophy is common, and use of cerebral glucose is reduced, as is perfusion in the parietal lobe, temporal cortices, and prefrontal cortex.

One of the characteristic pathological features of Alzheimer disease (AD) is a robust inflammatory response associated with extracellular deposition of amyloid β-protein (Aβ). Microglia are the predominant immune cells in the brain that participate in the inflammatory response in AD. Activation of microglia may contribute to the neurodegenerative process by the elaboration of proinflammatory cytokines, such as interleukin-1β, IL-6 and tumor necrosis factor-α, as well as other neurotoxic factors. Epidemiological studies indicate that there might be a reduced risk of AD in patients who have been treated with non-steroidal anti-inflammatory drugs, suggesting that inflammation may contribute to disease progression.

Amyotrophic lateral sclerosis (ALS): ALS (Lou Gehrig disease, Charcot's syndrome) is the most common motor neuron disease. Patients present with random, asymmetric symptoms, consisting of cramps, weakness, and muscle atrophy of the hands (most commonly) or feet. Fasciculations, spasticity, hyperactive deep tendon reflexes, extensor plantar reflexes, clumsiness, stiffness of movement, weight loss, fatigue, and difficulty controlling facial expression and tongue movements soon follow. Other symptoms include hoarseness, dysphagia, slurred speech, and a tendency to choke on liquids. Late in the disorder, inappropriate, involuntary, and uncontrollable excesses of laughter or crying (pseudobulbar affect) occur. Death is usually caused by failure of the respiratory muscles.

Experimental evidence supports a model for ALS neurodegeneration in which nonneuronal cells such as microglia contribute to the demise of motor neurons. Over the course of the disease, spinal cord microglial cells may become activated and acquire the capacity of oxidatively damaging nearby macromolecules and cells homed within inflamed ALS tissues. Evidence of microgliosis, NADPH oxidase upregulation, and protein carbonylation has also been found in postmortem spinal cords from human sporadic ALS cases, supporting the conclusion that the occurrence of inflammation-mediated oxidative damage is also a pathological hallmark of the prevalent nonfamilial, sporadic form of ALS.

Rheumatoid Arthritis is a chronic syndrome characterized by usually symmetric inflammation of the peripheral joints, potentially resulting in progressive destruction of articular and periarticular structures, with or without generalized manifestations. The cause is unknown. A genetic predisposition has been identified and, in white populations, localized to a pentapeptide in the HLA-DR beta1 locus of class II histocompatibility genes. Environmental factors may also play a role. Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint.

SLE. Systemic lupus erythematosus (SLE) is an autoimmune disease characterized by polyclonal B cell activation, which results in a variety of anti-protein and non-protein autoantibodies (see Kotzin et al. (1996) Cell 85:303-306 for a review of the disease). These autoantibodies form immune complexes that deposit in multiple organ systems, causing tissue damage. SLE is a difficult disease to study, having a variable disease course characterized by exacerbations and remissions. For example, some patients may demonstrate predominantly skin rash and joint pain, show spontaneous remissions, and require little medication. The other end of the spectrum includes patients who demonstrate severe and progressive kidney involvement (glomerulonephritis) that requires therapy with high doses of steroids and cytotoxic drugs such as cyclophosphamide.

Multiple factors may contribute to the development of SLE. Several genetic loci may contribute to susceptibility, including the histocompatibility antigens HLA-DR2 and HLA-DR3. The polygenic nature of this genetic predisposition, as well as the contribution of environmental factors, is suggested by a moderate concordance rate for identical twins, of between 25 and 60%.

Many causes have been suggested for the origin of autoantibody production. Proposed mechanisms of T cell help for anti-dsDNA antibody secretion include T cell recognition of DNA-associated protein antigens such as histones and recognition of anti-DNA antibody-derived peptides in the context of class II MHC. The class of antibody may also play a factor. In the hereditary lupus of NZB/NZW mice, cationic IgG2a anti-double-stranded (ds) DNA antibodies are pathogenic. The transition of autoantibody secretion from IgM to IgG in these animals occurs at the age of about six months, and T cells may play an important role in regulating the IgG production.

Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter is the association between anti-neuronal antibodies and neuropsychiatric SLE.

Atherosclerosis. Atherosclerotic plaque consists of accumulated intracellular and extracellular lipids, smooth muscle cells, connective tissue, and glycosaminoglycans. Macrophages are integral to the development of atherosclerosis. The modified or oxidized LDL is chemotactic to monocytes, promoting their migration into the intima, their early appearance in the fatty streak, and their transformation and retention in the subintimal compartment as macrophages. Scavenger receptors on the surface of macrophages facilitate the entry of oxidized LDL into these cells, transferring them into lipid-laden macrophages and foam cells. Oxidized LDL is also cytotoxic to endothelial cells and may be responsible for their dysfunction or loss from the more advanced lesion.

The chronic endothelial injury hypothesis postulates that endothelial injury by various mechanisms produces loss of endothelium, adhesion of platelets to subendothelium, aggregation of platelets, chemotaxis of monocytes and T-cell lymphocytes, and release of platelet-derived and monocyte-derived growth factors that induce migration of smooth muscle cells from the media into the intima, where they replicate, synthesize connective tissue and proteoglycans, and form a fibrous plaque. Other cells, e.g. macrophages, endothelial cells, arterial smooth muscle cells, also produce growth factors that can contribute to smooth muscle hyperplasia and extracellular matrix production.

Endothelial dysfunction includes increased endothelial permeability to lipoproteins and other plasma constituents, expression of adhesion molecules and elaboration of growth factors that lead to increased adherence of monocytes, macrophages and T lymphocytes. These cells may migrate through the endothelium and situate themselves within the subendothelial layer. Foam cells also release growth factors and cytokines that promote migration of smooth muscle cells and stimulate neointimal proliferation, continue to accumulate lipid and support endothelial cell dysfunction. Clinical and laboratory studies have shown that inflammation plays a major role in the initiation, progression and destabilization of atheromas.

The "autoimmune" hypothesis postulates that the inflammatory immunological processes characteristic of the very first stages of atherosclerosis are initiated by humoral and cellular immune reactions against an endogenous antigen. Human Hsp60 expression itself is a response to injury initiated by several stress factors known to be risk factors for atherosclerosis, such as hypertension. Oxidized LDL is another candidate for an autoantigen in atherosclerosis. Antibodies to oxLDL have been detected in patients with atherosclerosis, and they have been found in atherosclerotic lesions. T lymphocytes isolated from human atherosclerotic lesions have been shown to respond to oxLDL and to be a major autoantigen in the cellular immune response. A third autoantigen proposed to be associated with atherosclerosis is 2-Glycoprotein I (2GPI), a glycoprotein that acts as an anticoagulant in vitro. 2GPI is found in atherosclerotic plaques, and hyper-immunization with 2GPI or transfer of 2GPI-reactive T cells enhances fatty streak formation in transgenic atherosclerotic-prone mice.

Infections may contribute to the development of atherosclerosis by inducing both inflammation and autoimmunity. A large number of studies have demonstrated a role of infectious agents, both viruses (cytomegalovirus, herpes simplex viruses, enteroviruses, hepatitis A) and bacteria (C. pneumoniae, H. pylori, periodontal pathogens) in atherosclerosis. Recently, a new "pathogen burden" hypothesis has been proposed, suggesting that multiple infectious agents contribute to atherosclerosis, and that the risk of cardiovascular disease posed by infection is related to the number of pathogens to which an individual has been exposed. Of single micro-organisms, C. pneumoniae probably has the strongest association with atherosclerosis.

These hypotheses are closely linked and not mutually exclusive. Modified LDL is cytotoxic to cultured endothelial cells and may induce endothelial injury, attract monocytes and macrophages, and stimulate smooth muscle growth. Modified LDL also inhibits macrophage mobility, so that once macrophages transform into foam cells in the subendothelial space they may become trapped. In addition, regenerating endothelial cells (after injury) are functionally impaired and increase the uptake of LDL from plasma.

Atherosclerosis is characteristically silent until critical stenosis, thrombosis, aneurysm, or embolus supervenes. Initially, symptoms and signs reflect an inability of blood flow to the affected tissue to increase with demand, e.g. angina on exertion, intermittent claudication. Symptoms and signs commonly develop gradually as the atheroma slowly encroaches on the vessel lumen. However, when a major artery is acutely occluded, the symptoms and signs may be dramatic.

Currently, due to lack of appropriate diagnostic strategies, the first clinical presentation of more than half of the patients with coronary artery disease is either myocardial infarction or death. Further progress in prevention and treatment depends on the development of strategies focused on the primary inflammatory process in the vascular wall, which is fundamental in the etiology of atherosclerotic disease.

Therapeutic Agents

In one embodiment of the invention, modulators of alpha B crystallin activity, e.g. αBC polypeptides, nucleic acids encoding αBC, and the like are used in the treatment of inflammatory disease, including rheumatoid arthritis, and demyelinating autoimmune disease, such as MS.

Alpha B crystallin polypeptides, which can be used in' the methods of the invention, comprise at least about 50 amino acids, usually at least about 100 amino acids, at least about 150 amino acids, at least about 160 amino acids, at least about 170 amino acids, and which may include up to 175 amino acids of an alpha B crystallin protein, or modifications thereof, and may further include fusion polypeptides as known in the art in addition to the provided sequences. The alpha B crystallin sequence may be from any mammalian or avian species, e.g. primate sp., particularly humans; rodents, including mice, rats and hamsters; rabbits; equines, bovines, canines, felines; etc. Of particular interest are the human proteins.

In some embodiments of the invention, the αBC protein, or a functional fragment thereof is administered to a patient. αBC polypeptides useful in this invention also include derivatives, variants, and biologically active fragments of naturally occurring αBC polypeptides, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

The sequence of alpha B crystallin peptides as described above may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins in a fusion protein, typically where the two proteins are not normally joined, such as the Fc of an IgG isotype, which may be complement binding, with a toxin, such as ricin, abrin, diphtheria toxin, or the like, or with specific binding agents that allow targeting to specific moieties on a target cell.

The αBC may be fused to another polypeptide to provide for added functionality, e.g. to increase the in vivo stability. Generally such fusion partners are a stable plasma protein, which may, for example, extend the in vivo plasma half-life of the αBC when present as a fusion, in particular wherein such a stable plasma protein is an immunoglobulin constant domain.

In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the αBC also will be produced and employed as a multimer having substantially the same structure as the stable plasma protein precursor. These multimers will be homogeneous with respect to the αBC they comprise, or they may contain more than one αBC.

Stable plasma proteins are proteins typically having about from 30 to 2,000 residues, which exhibit in their native environment an extended half-life in the circulation, i.e. greater than about 20 hours. Examples of suitable stable plasma proteins are immunoglobulins, albumin, lipoproteins, apolipoproteins and transferrin. The αBC typically is fused to the plasma protein, e.g. IgG at the N-terminus of the plasma protein or fragment thereof which is capable of conferring an extended half-life upon the αBC. Increases of greater than about 100% on the plasma half-life of the αBC are satisfactory. Ordinarily, the αBC is fused C-terminally to the N-terminus of the constant region of immunoglobulins in place of the variable region(s) thereof, however N-terminal fusions may also find use.

Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the αBC. For some embodiments fusions will containing αBC immune epitopes that are recognized by antibodies. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The alpha B crystallin for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the alpha B crystallin polypeptide consists essentially of a polypeptide sequence of at least 175 amino acids in length and having a sequence of an alpha B crystallin peptide as described above. By "consisting essentially of" in the context of a polypeptide described herein, it is meant that the polypeptide is composed of the alpha B crystallin sequence, which sequence is optionally flanked by one or more amino acid or other residues that do not materially affect the basic characteristic(s) of the polypeptide.

The invention includes nucleic acids encoding alpha B crystallin polypeptides. The nucleic acid sequences encoding the above alpha B crystallin polypeptides may be accessed from public databases. Identification of additional alpha B crystallins is accomplished by conventional screening methods of DNA libraries or biological samples for DNA sequences having a high degree of similarity to known alpha B crystallin sequences. Polynucleotides of interest include those that encode a polypeptide that consists essentially of a polypeptide sequence of at least about 50 amino acids, usually at least about 100 amino acids, at least about 150 amino acids, at least about 160 amino acids, at least about 170 amino acids, and which may include up to 175 amino acids of an alpha B crystallin protein. Such polynucleotides may be operably joined to, control sequences, e.g. for transcriptional start, stop, translation, promoters, etc. Polynucleotides may also include an alpha B crystallin coding sequence combined with fusion polypeptide sequences.

Alpha B crystallin coding sequences can be generated by methods known in the art, e.g. by in vitro synthesis, recombinant methods, etc. to provide a coding sequence to corresponds to an alpha B crystallin polypeptide that can serve as an intermediate in the production of the alpha B crystallin peptide. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

Alpha B crystallin encoding nucleic acids can be provided as a linear molecule or within a circular molecule, and can be provided within autonomously replicating molecules (vectors) or within molecules without replication sequences. Expression of the nucleic acids can be regulated by their own or by, other regulatory sequences known in the art. The nucleic acids can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce an alpha B crystallin coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The nucleic acid may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold microprojectiles are coated with the alpha B crystallin or DNA, then bombarded into skin cells.

The method also provide for combination therapy, where the combination may provide for additive or synergistic benefits. Combinations of alpha B crystallin may be obtained with a second agent selected from one or more of the general classes of drugs commonly used in the non-antigen specific treatment of autoimmune disease, which include corticosteroids and disease modifying drugs; or from an antigen-specific agent. Corticosteroids have a short onset of action, but many disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like.

Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying anti-rheumatoid drugs, or DMARDs have been shown to alter the disease course and improve radiographic outcomes in RA. It will be understood by those of skill in the art that these drugs are also used in the treatment of other autoimmune diseases.

Methotrexate (MTX) is a frequent first-line agent because of its early onset of action (4-6 weeks), good efficacy, favorable toxicity profile, ease of administration, and low cost. MTX is the only conventional DMARD agent in which the majority of patients continue on therapy after 5 years. MTX is effective in reducing the signs and symptoms of RA, as well as slowing or halting radiographic damage. Although the immunosuppressive and cytotoxic effects of MTX are in part due to the inhibition of dihydrofolate reductase, the anti-inflammatory effects in rheumatoid arthritis appear to be related at least in part to interruption of adenosine and TNF pathways. The onset of action is 4 to 6 weeks, with 70% of patients having some response. A trial of 3 to 6 months is suggested.

Antigen specific therapeutic methods include administration of an antigen or epitope specific therapeutic agent. In MS, the autoantibodies targeting alpha B crystallin (FIG. 5) may block αBC protective immunoinhibitory effects, and thereby exacerbate disease severity. As a result, an important therapeutic approach is to induce antigen-specific tolerance to alpha B crystalline, and thereby reduce autoreactive T cell. and autoantibody responses against alpha B crystallin. Reducing autoantibodies to alpha B-crystallin would (i) reduce autoimmune damage to the myelin sheath, and (ii)

enable this negative regulator to inhibit pathogenic immune responses and tissue destruction, and thereby provide benefit in MS.

One method to induce immune tolerance is tolerizing DNA vaccines (Garren et al. (2001) Immunity, 15:15-22; Robinson et al. (2003) Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of alpha B crystallin in order to induce immune tolerance to the encoded epitopes. To enhance the ability of such plasmids to induce immune tolerance, the immunostimulatory CpG sequences (Krieg et al. (1998) Trends Microbiol. 6:23-27) can be reduced in number or completely removed from the plasmid vector. Additionally, immunoinhibitory GpG sequences can be added to the vector (see Ho et al. (2005) J. Immunology, 175:6226-34). Tolerizing DNA plasmids encoding alpha B crystallin are delivered intramuscularly to induce immune tolerance to alpha B crystallin, thereby reducing anti-alpha B crystallin T cell and autoantibody responses to reduce autoimmune destruction of the myelin sheath and to reduce antibodies blocking the protective effects of alpha B crystallin.

As an alternative, or in addition to DNA tolerization, specific peptides, altered peptides, or proteins may be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Pharmaceutical Compositions

Active polypeptides or polynucleotides can serve as the active ingredient in pharmaceutical compositions formulated for the treatment of various disorders as described above. The active ingredient is present in a therapeutically effective amount, i.e., an amount sufficient when administered to substantially modulate the effect of the targeted protein or polypeptide to treat a disease or medical condition mediated thereby. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which are composed of the packaged active ingredient with a suppository base. Suitable suppository bases include natural or synthetic triglycerides or paraffin hydrocarbons. In addition, it is also possible to use gelatin rectal capsules, which are composed of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

Modulation of Alpha B Crystallin Expression

Alpha B crystallin genes, gene fragments, or the encoded protein or protein fragments are useful in gene therapy to treat inflammatory disease. Expression vectors may be used to introduce an alpha B crystallin coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more preferably for a period of at least about several days to several weeks.

The gene may be introduced into tissues or host cells by any number of routes, including viral infection, microinjection, or fusion of vesicles. Jet injection may also be used for intramuscular administration, as described by Furth et al. (1992) *Anal Biochem* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the DNA, then bombarded into skin cells.

Methods of Treatment

The αBC compositions may be administered in a single dose, or in multiple doses, usually multiple doses over a period of time, e.g. daily, every-other day, weekly, semi-weekly, monthly etc. for a period of time sufficient to reduce severity of the inflammatory disease, which may comprise 1, 2, 3, 4, 6, 10, or more doses.

Determining a therapeutically or prophylactically effective amount an agent that provides αBC activity can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of nucleic acid or protein, as applicable. In a further embodiment, the effective amount contains between about 10 mg and about 50 mg of the nucleic acid or protein, as applicable. The effective dose will depend at least in part on the route of administration. The agents may be administered orally, in an aerosol spray; by injection, e.g. i.m., s.c., i.p., i.v., etc. In some embodiments, administration by other than i.v. may be preferred. The dose may be from about 0.1 µg/kg patient weight; about 1 µg/kg; about 10 µg/kg; to about 100 µg/kg.

The αBC compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of αBC compositions of the invention in the pharmaceutical formulations can vary widely, i.e. from less than about 0.1%, usually at or at least about 2% to as much as 20% to 50% or more by weight, and will be selected primarily by fluid volumes, viscosities, etc:, in accordance with the particular mode of administration selected.

Treating, treatment, or therapy of a disease or disorder shall mean slowing, stopping or reversing the disease's progression by administration of an αBC composition. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration of an αBC composition to prevent the occurrence or onset of a disease or disorder or some or all of the symptoms of a disease or disorder or to lessen the likelihood of the onset of a disease or disorder.

This invention will be better understood by reference to the Examples which follow, but those skilled in the art will readily appreciate that the information detailed is only illustrative of the invention as, described more fully in the claims which follow thereafter.

EXPERIMENTAL

Results

Figure 7:
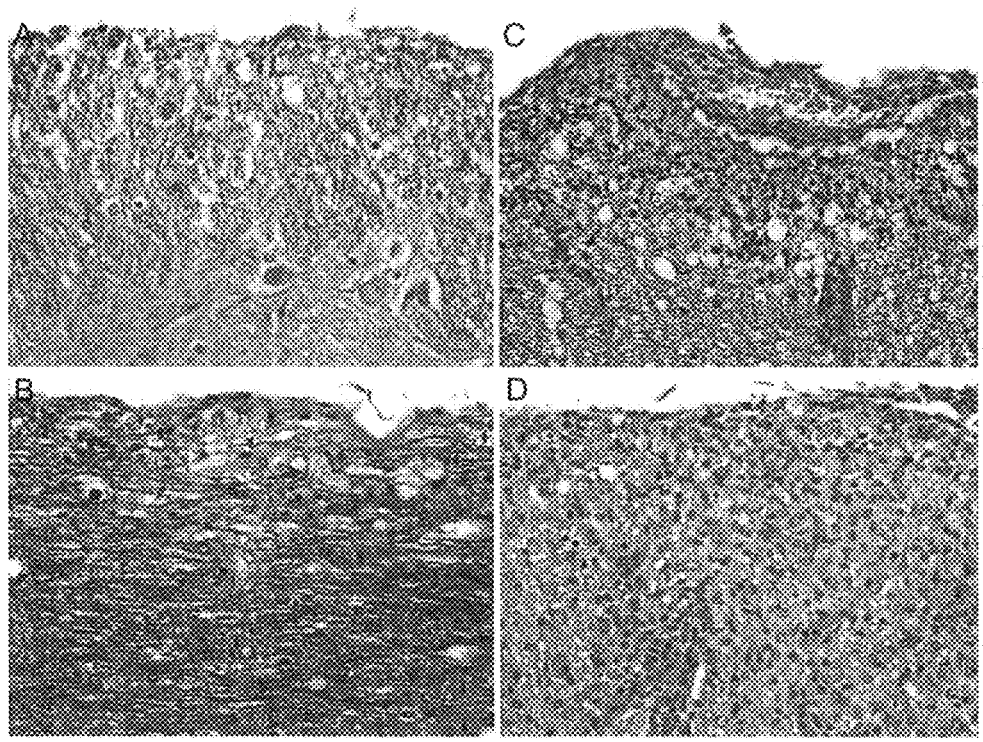
FIG. 7. $\alpha BC^{-/-}$ mice have more severe inflammation/demyelinating lesions in acute and progressive EAE. Paraffin-embedded spinal cord sections taken at day 14 (A,C) and day 42 (B, D) from WT (A, B) and $\alpha BC^{-/-}$ (C, D) animals with EAE and stained with luxol fast blue and hematoxylin-eosin. 1640×magnification.

We first examined EAE in αBC null mice (αBC$^{-/-}$) mice immunized with MOG 35-55 in CFA. These mice displayed more severe clinical EAE, particularly at peak disease and at later phases of the disease compared to 129S6 wild-type (WT) animals (FIG. 1A). This difference was associated with more severe inflammation and demyelination in the brain and spinal cord of the αBC null animals both in the acute (day 14) and progressive phases of disease (day 42) (Table 1, FIG. 7).

TABLE 1

Quantification of inflammatory infiltrates in brain and spinal cord of WT and αBC$^{-/-}$ mice with EAE.

|  | Meninges | Parenchyma | Total |
|---|---|---|---|
| Day 14 |  |  |  |
| WT | 59 ± 17.6 | 49.5 ± 12.3 | 108.5 ± 29.1 |
| αBC$^{-/-}$ | 127.6 ± 17.7* | 116.4 ± 7.2* | 234 ± 17.7* |
| Day 42 |  |  |  |
| WT | 20 ± 10.1 | 21 ± 11.1 | 41 ± 11.1 |
| αBC$^{-/-}$ | 135 ± 25.1* | 151 ± 49.1* | 286 ± 24.1* |

Figure 1:
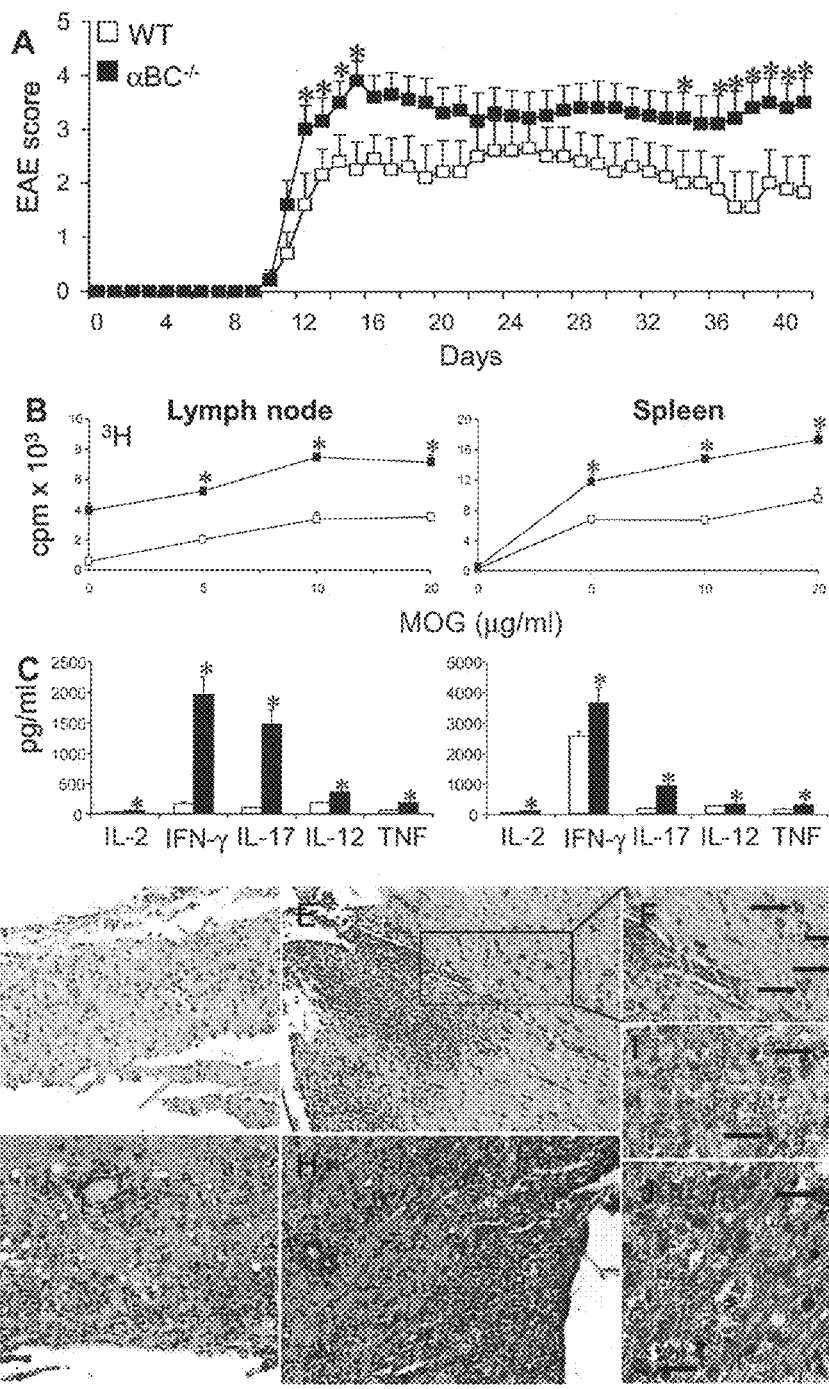
FIG. 1. $\alpha BC^{-/-}$ mice developed worse clinical EAE with increased immune cell activation, CNS inflammation and glial cell death. (A) Mean±s.e.m. clinical scores of WT (□) and $\alpha BC^{-/-}$ (■) mice at various days after immunization with MOG 35-55.* indicates a significant difference from WT group (p<0.05) as determined by Mann-Whitney U statistic. (B) Proliferation rate and (C) secretion of pro-inflammatory cytokines IFN-γ, TNF, IL-2, IL-12p40, IL-17 by lymph node cells and splenocytes from WT (□) and $\alpha BC^{-/-}$ (■) mice with EAE. (D-J) Paraffin-embedded spinal cord sections taken at day 42 from WT (D, G, I) and $\alpha BC^{-/-}$ (E-F, H, J) animals with EAE and immuno-stained for cleaved (D-F), uncleaved caspase-3 (G, H) and TUNEL (I, J). (D-E, G-H) 20×; (F) 40×; (I, J) 75×magnification. Arrows point to glial cells immuno-positive for cleaved caspase-3 (F) and TUNEL (I, J) staining.
Figure 8:
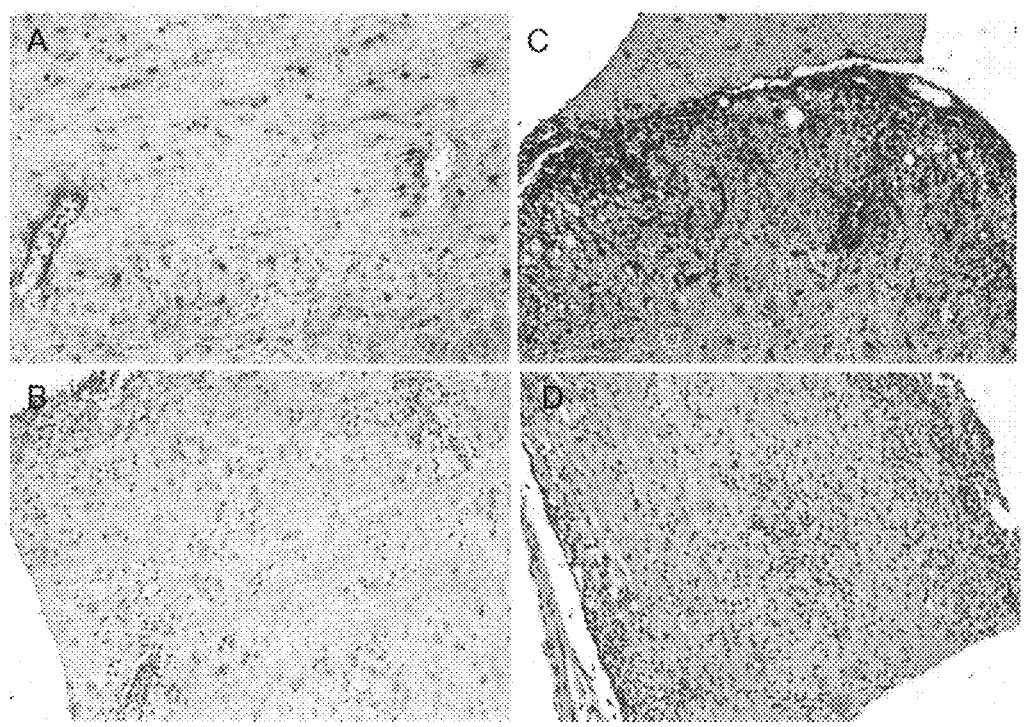
FIG. 8. $\alpha BC^{-/-}$ mice have higher expression of cleaved caspase-3 in acute EAE.

Values are means (s.e.m);
*denotes a significant difference from WT counterpart, $p < 0.05$; $n = 4$ To determine whether there was more cell death that may have contributed to the worsened disease in αBC$^{-/-}$ animals, we immunostained brains and spinal cords from WT and αBC$^{-/-}$ null EAE mice for cleaved and uncleaved caspase-3. Compared to WT animals, mice lacking αBC expression had more immunostaining for uncleaved caspase-3 (FIG. 1G-H) in inflammatory lesions in the brain, and particularly in spinal cord at both the acute (day 14) (FIG. 8) and later stage (day 42) (FIG. 1 G-H) of EAE. Cleaved caspase-3 expression was only observed at day 42 in both WT and αBC$^{-/-}$ mice with EAE. The αBC$^{-/-}$ mice showed more staining of cells with large nuclei and abundant cytoplasm that were morphologically consistent with glia in the white matter whereas few immune cells were immunopositive (FIG. 1 E, F). To correlate the cleaved caspase-3 expression with apoptosis, we performed TUNEL staining on the CNS tissues of mice with late stage EAE. Most TUNEL-positive cells in the WT animals with EAE showed typical dense nuclear staining (FIG. 1I), whereas TUNEL-positive cells in the αBC$^{-/-}$ mice were more numerous and a greater proportion of positive cells had more abundant cytoplasm staining, suggesting that they were glia (FIG. 1J). These results suggest that αBC may play a role in preventing apoptosis of glial cells in the CNS during EAE.

EAE is driven by pathogenic immune responses against myelin proteins and lipids. αBC may have an anti-inflammatory role. To determine whether the immune response to constitutively expressed myelin proteins was also affected in αBC$^{-/-}$ mice with EAE, we compared the proliferative ability and cytokine secretion of lymphoid cells from the spleen and lymph nodes from αBC$^{-/-}$ mice with that of WT animals. Splenocytes and lymph node cells from αBC$^{-/-}$ MOG-immunized mice displayed significantly higher proliferation and secretion of the Th1 cytokines IL-2, IFN-γ, TNF, IL-12p40 compared to WT animals (FIG. 1B, C). These cells from the null animals also secreted more IL-17 (FIG. 1C). No Th2 cytokines (IL-4 and IL-10) were detectable in these cell types from either αBC$^{-/-}$ or WT animals.

To determine the specific cells types that were hyper-responsive during EAE in αBC$^{-/-}$ mice, we assessed the proliferation capabilities and cytokine production of T cells and antigen-presenting cells (APCs) such as macrophages. Similar to splenocytes and lymph node cells, CD3$^+$ T cells from αBC$^{-/-}$ MOG-immunized mice stimulated with MOG 35-55 proliferated more (cpm) and secreted higher concentrations of IL-2, IFN-γ, and IL-17 (pg/ml) when compared to their WT counterparts (FIG. 2A). Naïve CD3$^+$ T cells from null animals also showed a similar hyper-responsiveness when stimulated in culture with anti-CD3 and anti-CD28.

Figure 3:
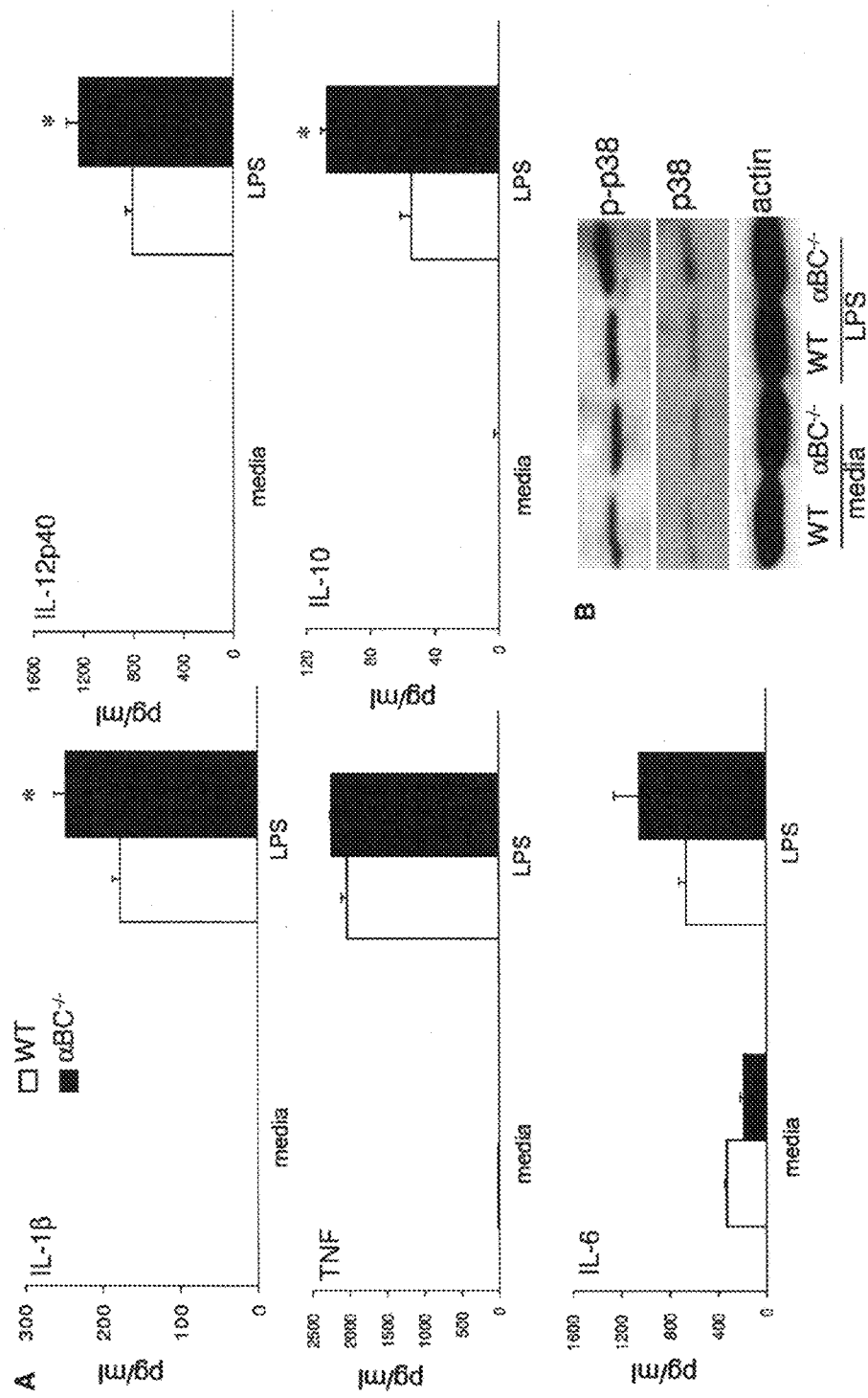
FIG. 3. Macrophages deficient in $\alpha BC$ are hyperactive. (A) Production of cytokines (IL-1β, TNF, IL-6, IL-12p40, IL-10) (pg/ml) by WT (□) and $\alpha BC^{-/-}$ (■) macrophages stimulated in vitro with LPS (B) Western blot analysis of p38 and phospho-p38 expression in WT and $\alpha BC^{-/-}$ null macrophages 72 h after stimulation with LPS.

To determine whether APC function was also affected, we isolated macrophages from thioglycollate treated WT and αBC$^{-/-}$ mice and stimulated them with LPS. Macrophages from the αBC$^{-/-}$ mice also showed increased capacities to secrete inflammatory cytokines, releasing more IL-12p40, IL-6 and IL-1β. There was no difference in TNF production. Interestingly, these cells also secreted more IL-10 (FIG. 3A).

Since the MAP kinase signal transduction pathways are involved in αBC function, we determined whether the JNK, ERK or p38 pathways played a role in the immune cell hyper-responsiveness seen in αBC$^{-/-}$ mice with EAE. We found that total and phosphorylated p38 expression was upregulated in stimulated αBC$^{-/-}$ CD3$^+$ T cells (FIG. 2B) and macrophages (FIG. 3B). There was no difference in expression of the JNK and ERK pathway molecules between WT and αBC$^{-/-}$ T cells and macrophages. These results demonstrated that the inflammatory response was hyperactive in αBC$^{-/-}$ animals and suggested that αBC may have a dampening role on both T cell and macrophage populations during EAE, though the dampening effect may be insufficient by itself to completely abrogate the disease.

Astrocytes use the canonical NF-κB pathway to modulate inflammation in EAE, and they upregulate expression of αBC during EAE and MS. We assessed whether the function of astrocytes is altered in αBC$^{-/-}$ mice. Primary astrocytes isolated from αBC$^{-/-}$ pups produced more IL-6 compared to WT astrocytes, 48 hours following either TNF or staurosporine stimulation (FIG. 4A). Since αBC is anti-apoptotic we assessed whether αBC$^{-/-}$ astrocytes underwent cell death at a different rate compared to WT astrocytes. αBC has been shown to protect cells from apoptosis by downregulating caspase-3 expression by binding pro-caspase-3. Naïve astrocytes from both WT and αBC$^{-/-}$ mice expressed caspase-3 after 4 weeks in culture. However, naïve astrocytes from αBC$^{-/-}$ mice showed differential expression of cleaved caspase-3 compared to WT cells, where this apoptotic factor remained uncleaved even after stimulation with TNF. In contrast, an additional small increase in cleaved caspase-3 was observed in αBC$^{-/-}$ cells 72 h following TNF stimulation (FIG. 4B). In addition, compared to WT cells a greater percentage of astrocytes from null animals displayed more TUNEL staining with and without TNF stimulation (FIG. 4C), suggesting that αBC protects astrocytes against normal cell death and during stress injury (FIG. 4C).

To determine the underlying signaling mechanism(s) mediating the increased cell death in the αBC$^{-/-}$ astrocytes, we assessed the expression of the MAP kinase signal transduction pathways involved with αBC function. Astrocytes from WT animals increased expression of αBC following 72 h TNF stimulation. These cells also showed a small increase in p-αBC (p59) expression but p-αBC (Ser 45) decreased slightly (FIG. 4B). No αBC was seen in null astrocytes. The p38 and ERK pathways are modulated by αBC in various cells. αBC prevents activation of the ERK pathway thereby inhibiting caspase-3 maturation and thus cell death[31]. We found that p-ERK and ERK were both upregulated in αBC$^{-/-}$ astrocytes 72 h after. TNF stimulation. WT astrocytes also increased expression of p-ERK although total ERK remained unchanged. p38 was also upregulated in null astrocytes after TNF stimulation but the phosphorylated form of this protein was not detected. No changes in JNK and p-JNK expression were seen in WT and αBC$^{-/-}$ astrocytes (not shown).

We then assessed whether the NF-κB pathway was modulated by αBC. Astrocytes null for αBC upregulated expression of the active subunits NF-κB p65 and NF-κB p105/p50 while down-regulating their negative regulator IκB-α following TNF stimulation (FIG. 4B). WT astrocytes on the other hand showed an increase in the IKB-α inhibitor and no NF-κB p50 was evident in this genotype even after TNF stimulation (FIG. 4B). NF-κB DNA binding assays confirmed an enhancement in NF-κB p50 and NF-κB p65 DNA binding activity in TNF-stimulated αBC$^{-/-}$ astrocytes compared to WT glial cells (FIG. 4D). Therefore, αBC prevents cell death of astrocytes by inhibiting caspase-3 activation, and suppressing the inflammatory role of NF-κB in astrocytes during demyelinating disease.

Figure 5:
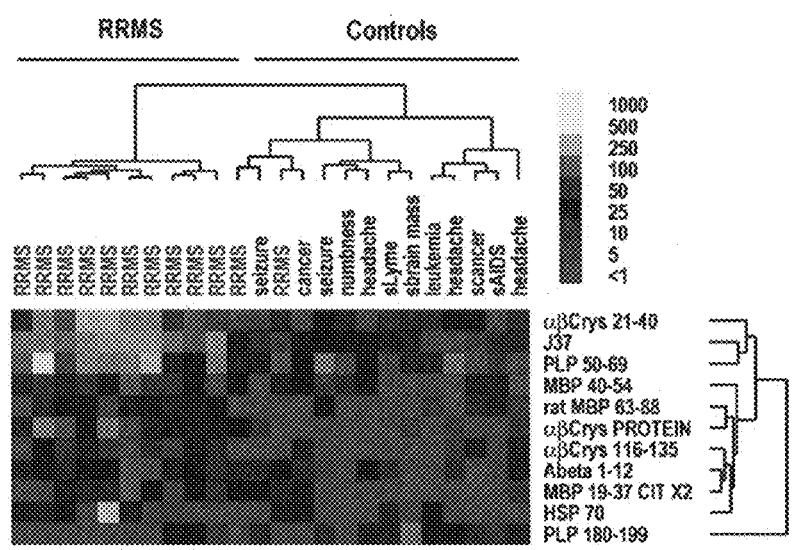
FIG. 5. Myelin antigen array analysis demonstrates antibody targeting of αBC in human RRMS patients. Myelin array analysis was performed on CSF derived from RRMS and OND control patients. The statistical algorithm SAM was applied to identify significant differences in antibody reactivity in RRMS as compared to OND control samples, and the samples and myelin antigen hits arranged using a hieratical clustering algorithm, and results displayed as a heat map. RRMS patients demonstrated significantly increased autoantibody reactivity against a variety of myelin epitopes including DBC protein and peptides.

We have constructed large scale arrays to detect autoantibodies to various myelin antigens, including full length αBC, and a number of its peptide epitopes. In EAE, antibody to epitopes p16-35, p26-45 and p116-135 on αBC appears within 17 days in the sera after immunization with PLPp139-151. In multiple sclerosis, we applied myelin antigen arrays to analyze antibody to αBC in the cerebrospinal fluid of patients with relapsing remitting MS (RRMS). Antibodies to native αBC and to p21-40 and p116-135 of αBC were prominently detected (FIG. 5).

Figure 6:
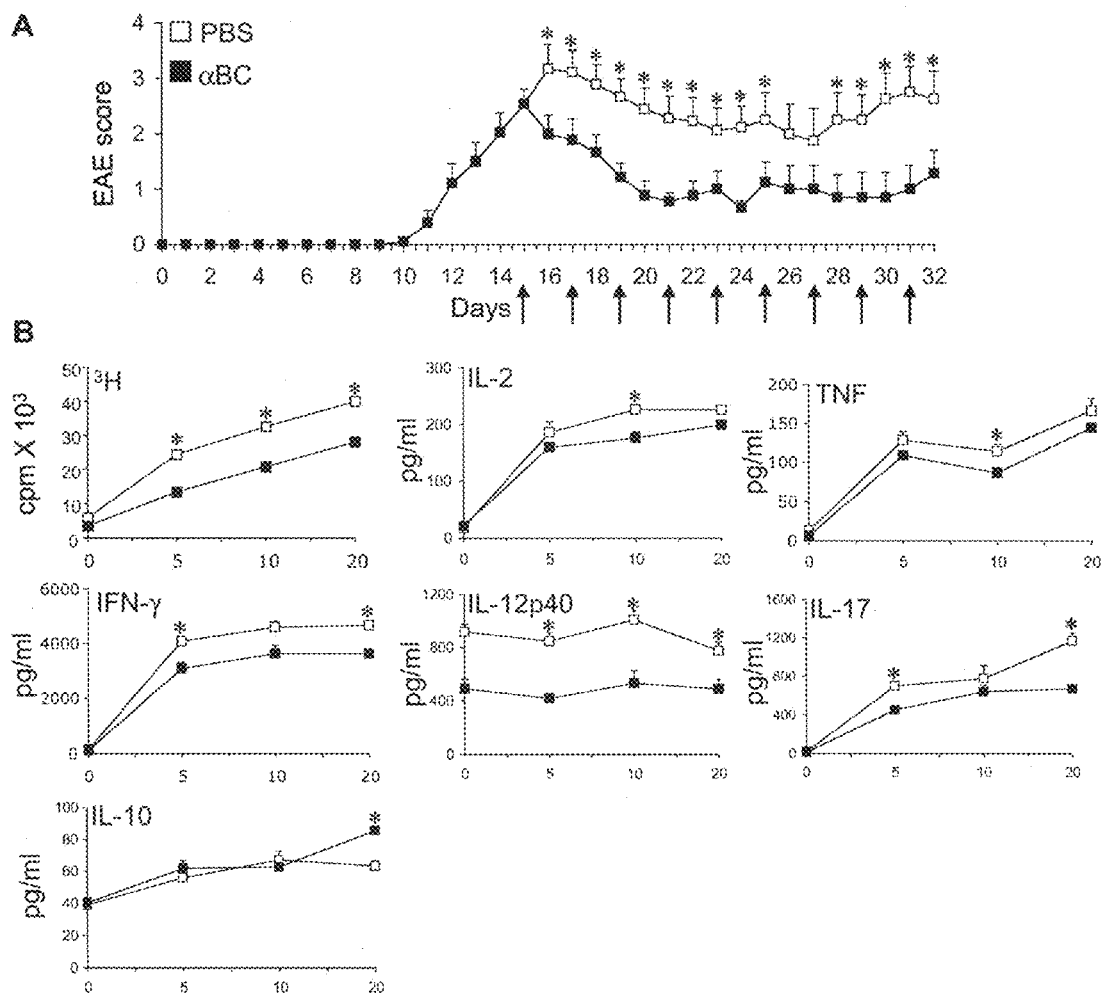
FIG. 6. Recombinant αBC suppresses clinical disease and inflammation in EAE. (A) Mean clinical scores of WT EAE mice treated with recombinant αBC (■) or PBS pH 7.0 (□) at various days following immunization with MOG 35-55 and pertussis toxin. (B) Proliferation rate (cpm) and cytokine (pg/ml) production of splenocytes taken at day 25 of EAE during recombinant αBC (■) or PBS (□) treatment. * indicates a significant difference from WT group (p<0.05) as determined by Mann-Whitney U statistic.

Our results indicated that αBC has both a suppressive effect on immune cell function and an anti-apoptotic role in CNS glial cells. To show that antibody to αBC from the CSF of MS patients worsened EAE, would be complicated by the fact that in EAE there are already antibodies to αBC that arise as a result of epitope spreading, as we and others have shown earlier. Therefore it would be difficult to transfer antibody from human CSF to mice, in a manner similar to experiments performed nearly thirty years ago showing that the immunoglobulin in myasthenia gravis patients could be transferred to mice, who then became myasthenic. We therefore assessed whether recombinant αBC itself could resolve disease in mice with ongoing EAE. To test this, we treated WT mice with EAE every two days with 10 μg of recombinant human αBC administered intravenously. Mice treated with αBC showed significantly lower clinical disease compared to PBS-injected animals (FIG. 6A). This amelioration of disease was due in part to decreased infiltration of immune cells into the brain and spinal cord (Table 2) and, suppression of immune cell function (FIG. 6B). We observed decreased proliferation and, production of Th1 (IL-2, IL-12p40, TNF, IFN-γ) and IL-17 cytokines by splenocytes taken from mice treated with recombinant αBC (FIG. 6B). Interestingly, increased production of the immune suppressive cytokine, IL-10, was observed at high concentrations of MOG stimulation (FIG. 6B). A decrease in immune cell function was similarly observed in CD3+ T cells stimulated in vitro with anti-CD3/anti-CD28 and treated with recombinant αBC.

To assess whether αBC treatment affected cell death in the CNS we performed TUNEL staining on brain and spinal cord sections from the PBS and αBC-treated mice with EAE. Less TUNEL staining was observed in the CNS parenchyma in mice treated with αBC compared to PBS-injected animals (Table 2; FIG. 9). In addition, fewer cells with diffuse TUNEL staining suggestive of dying glial cells were seen in the CNS of the crystallin-treated animals suggesting a protective effect on glia of exogenously administered recombinant αBC.

TABLE 2

Quantification of inflammatory infiltrates and TUNEL positive cells in brain and spinal cord of WT mice with EAE treated with PBS and recombinant αBC.

|  | Meninges | Parenchyma | Total | TUNEL |
| --- | --- | --- | --- | --- |
| PBS | 115.3 ± 31.8 | 107.7 ± 28.3 | 223 ± 60.1 | 487.1 ± 104.1 |
| recombinant αBC | 48.7 ± 19.8* | 52 ± 38.5* | 100.7 ± 55.8* | 152.7 ± 74* |

Values are means (s.e.m);
*denotes a significant difference from WT counterpart, p < 0.05; n = 3

Responses to injury often are accompanied by protective mechanisms that serve to either antagonize the damaging events or to mediate the repair process. This concept is relevant in autoimmune demyelinating diseases such as MS, where the current and experimental treatment strategies primarily aim to decrease immunological activity and hence reduce inflammation. In MS, in addition to suppressing the pathological inflammatory response, it is also important to protect CNS cells from further damage and/or to induce repair when neurons and glial precursor cells are targeted for injury and death. Our findings show that αBC is a negative regulator that acts as a brake on several inflammatory pathways including the p38 kinase pathway in immune cells and also the caspase 3-mediated cell death pathway in glial cells. Of note, in a study of gene transcripts unique to MS lesions, αBC was the most abundant. αBC was also identified as the component of myelin from the brains of MS patients that triggered the strongest T cell response in MS patients. We, and others, have shown that antibody responses to αBC are seen in sera from animals with EAE and from MS patients (Robinson et al. (2003) Nat Biotechnol 21, 1033-9), and now show that antibody responses to αBC are present in the cerebrospinal fluid of MS patients.

Paradoxically perhaps, αBC not only suppresses T cell and macrophage proliferation and pro-inflammatory cytokine production via the p38 signal transduction pathway, but also inhibits death of glial cells and immune cell infiltration in the CNS in EAE. The capacity of αBC to protect glial cells from caspase-3-mediated cell death was mediated through the ERK and NF-κB pathways. These anti-inflammatory and pro-survival functions of αBC likely contribute to its therapeutic properties in reversing EAE.

Although αBC is highly upregulated in the CNS during MS and EAE its protective role may be overwhelmed by the inflammatory response, or there may be a disruption of αBC function. The antibodies present in the sera of MS patients (van Noort et al. (2006) Mult Scler 12, 287-93), and in the serum of mice with EAE, might indeed impair the function of αBC, interfering with its protective properties. Vigorous responses involving both T cell recognition of αBC, as well as the antibody responses to αBC shown here in the spinal fluids of MS patients, mean that adaptive immunity could suppress the activity of αBC in MS patients, impairing a key protective mechanism. We sought to see if administration of αBC itself would ameliorate ongoing EAE. Remarkably, administration of αBC itself was therapeutic.

One of the main adaptive immunological responses in MS and its animal model, EAE, is thus directed to an inducible stress protein, αBC. Such an immune response targeting a negative regulator of brain inflammation is comparable to damaging the braking system of a vehicle that is already careening into danger. Remarkably, addition of that very same stress protein, akin to restoring the brakes that were failing, returns control. αBC, a negative regulator of inflammation in EAE and MS brain, and a potent modulator of glial apoptosis, is apparently at a very critical tipping point in the pathophysiology of MS.

Methods

Mice. αBC null mice (αBC$^{-/-}$) were developed at the NIH National Eye Institute. These mice were generated from ES cells with a 129S4/SvJae background and maintained in 129S6/SvEvTac X 129S4/SvJae background. αBC$^{-/-}$ mice are viable and fertile, with no obvious prenatal defects and normal lens transparency. Older mice show postural defects and progressive myopathy that are apparent at approximately 40 weeks of age. We studied these mice between 8-12 weeks thus removing the possible effects of myopathy on our clinical evaluation. 129S6/SvEvTac (Taconic Farms) mice were used as controls. Colonies of VVT and αBC$^{-/-}$ mice were maintained in our animal colony and bred according to Stanford University Comparative Medicine guidelines.

EAE induction. EAE was induced in 8-12 week old female αBC$^{-/-}$ and WT 129S6/SvEvTac animals via subcutaneous immunization with 100 μg myelin oligodendrocyte. glycoprotein (MOG p35-55) peptide in an emulsion mixed (volume ratio 1:1) with Complete Freund's Adjuvant (containing 4 mg/ml of heat-killed Mycobacterium tuberculosis H37Ra, Difco Laboratories). Mice were also injected intravenously with 50 ng of Bordetella pertussis toxin (BPT) (Difco Laboratories) in PBS at the time of, and two days following immunization. MOG p35-55 peptide was synthesized by the Stanford Pan Facility and purified by high performance liquid chromatography (HPLC). Mice (n=8-10 per group) were examined daily for clinical signs of EAE and were scored as followed: 0=no clinical disease, 1=limp tail, 2=hindlimb weakness, 3=complete hindlimb paralysis, 4=hindlimb paralysis plus some forelimb paralysis, and 5=moribund or dead. All animal protocols were approved by the Division of Comparative Medicine at Stanford University and animals were maintained in accordance with the guidelines of the National Institutes of Health.

Histopathology. Brains and spinal cords were dissected from mice, fixed in 10% formalin in PBS and embedded in paraffin. Seven micron thick sections were stained with haematoxylin and eosin to detect inflammatory infiltrates and luxol fast blue for demyelination. Inflammatory lesions in brain, thoracic and lumbar spinal cord sections were counted by an examiner masked to the treatment status of the animal.

Astrocyte culture. Astrocytes were derived from the brains of 2-day-old αBC$^{-/-}$ and WT pups. Briefly, the cerebral cortices from three pups of each genotype were dissected and placed in modified Dulbecco's modified Eagle's medium (Invitrogen, Carlsbad, Calif.) containing penicillin-streptomycin-L-glutamine (Invitrogen). The meninges were removed and the cortices placed in 1 ml of complete Dulbecco's modified Eagle's medium (DMEM) containing 10% fetal bovine serum, 2 mM L-glutamine, 1 mM sodium pyruvate, 0.1 mM non-essential amino acids, 100 U/ml penicillin, 0.1 mg/ml streptomycin, (Invitrogen). The cortices were minced, vortexed at high speed for 1 min, and passed though an 18.5-gauge needle. The ensuing mixture was filtered successively through sterile 80-μm and 11-μm filters (Millipore, Bedford, Mass.) using a 25-mm Swinnex syringe filter holder (Millipore). The filtered cells were then diluted up to 1 ml with complete DMEM, plated into three 75-cm2 tissue culture flasks containing 10 ml of complete DMEM, and placed in a 5% aerated CO2 incubator kept at 37° C. Confluent astrocytes were stimulated with 100 ng/ml recombinant TNF (BioSource, Camarillo, Calif.) or 100 nM staurosporine (Sigma, Saint Louis, Mich.) and the cells and supernatants harvested for ELISA and Western blot analysis following stimulation.

Immune Cell Activation Assays and Cytokine Analysis. Splenocytes and lymph node cells ($5 \times 10^5$ cells/well) or CD3$^+$ T cells ($5 \times 10^4$ cells/well; purified by negative selection, R&D Systems, Minneapolis, Minn.) were cultured in flat-bottomed, 96-well plates in media (RPMI 1640 supplemented with 2 mM L-glutamine, 1 mM sodium pyruvate, 0.1 mM non-essential amino acids, 100 U/ml penicillin, 0.1 mg/ml streptomycin, 0.5 μM 2-mercaptoethanol, and 10% fetal calf serum) with MOG p35-55 peptide (5-20 μg/ml). To determine in vivo T cell function CD3+ T cells were purified from the spleens and lymph nodes of day 9 MOG-immunized mice and cultured 1:5 with irradiated syngeneic splenocytes and MOG p35-55 peptide (5-20 μg/ml).

Primary macrophages were isolated from the peritoneal cavity of αBC-/- and WT mice 3 days after intraperitoneal injection with 3 ml of 3% (w/v) thioglycollate (BD Diagnostics Systems, Sparks, Md.) and cultured ($1 \times 10^6$ cells/ml) with media alone (DMEM supplemented with 10% FCS, 1 mM sodium pyruvate, 100 U/ml penicillin, and 0.1 mg/ml streptomycin) in 24-well plates for 72 h and then activated with 100 ng/ml of LPS.

To assess proliferation rate, cultures were pulsed with [$^3$H] thymidine (1 μCi/well) after 72 h of culture and harvested 18 h later onto filter paper. The counts per minute (cpm) of incorporated [$^3$H] thymidine were read using a beta counter: Cytokines were measured in the supernatants of cultured cells using anti-mouse OPTEIA ELISA kits (BD Pharmingen, San Diego, Calif.). Supernatants were taken at the time of peak production for each cytokine (48 h: IL-2, IL-12p40, IL-6, IL-1β; 72 h: IFN-γ, TNF4; 96 h: IL-17; 120 h: IL-4, IL-10).

Recombinant αBC treatment. WT mice were induced with EAE using MOG 35-55 and pertussis toxin. When mice had hindlimb paralysis animals were divided into two groups balanced for mean clinical disease scores, and then injected intravenously every second day with saline, pH 7.0, or 10 μg recombinant human αBC (US Biological, Swampscott, Mass.) diluted in saline. To determine the effect of αBC treatment on immune cell function during EAE splenocytes were isolated during the remission phase, and stimulated in vitro with MOG 35-55.

Western Blot Analysis. CD3+ T cells, macrophages and astrocytes were lysed in 50 mM Tris-HCl buffer, pH 7.4, containing 1% NP-40, 10% glycerol, 1 mM EDTA, 1 mM Na3VO4, 1 mM NaF, 1 mM DTT, 4.5 mM Na pyrophosphate, 10 mM beta-glycerophosphate, and a protease inhibitor cocktail tablet (Roche Diagnostics, Penzberg, Germany). The supernatants were collected after centrifugation at 13,000 rpm at 4° C. for 30 min, and protein content determined with a spectrophotometer using absorption at 280 nM. Protein lysates (30-50 μg) were suspended in two volumes of double strength sodium dodecyl sulfate (SDS) Sample Buffer (Bio-Rad Laboratories, Hercules, Calif.) and subjected to SDS-PAGE electrophoresis using 10 or 15% Tris-HCl Ready Gels (Bio-Rad Laboratories). Proteins were transferred to PVDF membranes and blocked with 5% nonfat dried milk in 20 mM Tris-HCl-buffered saline (TBS), pH 7.4, containing 0.05% Tween-20. Membranes were immunoblotted 1:500 with the following antibodies overnight at 4° C.: p-αBC (Ser 45), p-αBC (Ser 59), αBC (StressGen BioReagents, Victoria, Canada); actin (Sigma); p-p38, p38, p-ERK, ERK, p-SAPK/JNK, SAPK/JNK, caspase-3, NFκBp105/p50, NF-κBp65, IκB-α (Cell Signaling Technology, Danvers, Mass.). Membranes were washed three times for 15 minutes with TBS buffer containing 0.1% Tween-20. Bound antibodies were visualized using peroxidase-conjugated secondary antibody (Amersham, Buckinghamshire, England) followed by detection using an ECL kit (Pierce, Rockford, Ill.). For reblotting, the membrane was first stripped in buffer (62.5 mM Tris-HCl, pH 6.8, with 2% SDS and 100 mM β-mercaptoethanol) for 1 h at 50° C.

Immunohistochemistry. Paraffin-embedded sagittal sections (7 μm) were hydrated and treated for antigen retrieval using 10 mM sodium citrate. Sections were incubated in 1% hydrogen peroxide to quench endogenous peroxidase, blocked in 1% BSA in PBS for 1 h at room temperature, and incubated overnight at 4° C. with caspase-3 (1:50) or cleaved caspase-3 (1:400) (Cell Signaling). Bound antibody was detected using Vectastain ABC anti-rabbit kits (Vector Laboratories, Burlingame, Calif.) and 3,5-diaminobenzidine (DAB)/$H_2O_2$ reagent as substrate. Before mounting, sections were counterstained with Mayer's hematoxylin and dehydrated in graded ethanols. To detect for apoptosis using the TUNEL method we used the ApopTag peroxidase in situ apoptosis detection kit according to the manufacturer's directions for paraffin-embedded sections (Chemicon, Temecula, Calif., USA).

NF-κB binding assay. WT and αBC$^{-/-}$ astrocytes were stimulated with 100 ng/ml TNF (BioSource, Camarillo, Calif.) for 72 h and nuclear protein extracts isolated using Clontech Laboratories' Transfactor Extraction kit. NF-κB p50 and NF-κB DNA binding was detected with 15 µg of nuclear protein using Clontech Transfactor Family Colorimetric kit-NF-κB.

Myelin arrays. Myelin antigen arrays were printed and probed as previously described. Briefly, proteins and peptides representing candidate myelin autoantigens were printed in ordered arrays on the surface of SuperEpoxy microscope slides (TeleChem, Mountain View, Calif.). Myelin arrays were probed with 1:20 dilutions of cerebral spinal fluid (CSF) derived from relapsing remitting MS (RRMS) or other neurologic disease (OND) control patients, followed by Cy-3-conjugated anti-human IgG/M secondary antibody (Jackson Immunoresearch). Arrays were scanned, and fluorescence quantitated as a measure of autoantibody binding.

Statistical Analysis. Data are presented as means±s.e.m. When data were parametric (kurtosis and skewness<2) and group variances homogenous (Bartlett homogeneity test), a one-way analysis of variance and Scheffé post-hoc test (for >2 groups) or a t-test (N=2 groups) were used to detect between-group differences. When data were non-parametric, ranks were compared amongst groups using a Kruskal-Wallis test and non-parametric test for multiple comparisons (for >2 groups) or a Mahn-Whitney U test (N=2 groups). A value of P<0.05 was considered significant. Myelin array results were analyzed using Significance Analysis of Microarrays (SAM) to identify antigen features with significant differences in antibody reactivity. These antigen 'hits' and the patient samples were then ordered using a hierarchical clustering algorithm and the results displayed as a heatmap using TreeView software.

Example 2

The mitogen activated protein kinases, known as MAP kinases, are key players in inflammation. Both p38 Map K and extracellular signal-regulated kinases ERK are key in the inflammatory response and have been shown to play a key role in the pathogenesis of myocardial infarction, stroke, and peripheral arterial ischemia, Alzheimer's Disease, Parkinson's Disease and Amyotrophic Lateral Sclerosis. For example gamma interferon regulation is controlled by p38 MapK and ERK signaling, shown in FIG. 10.

We have shown that the absence of aBC influences the p38 MapK and ERK pathways in brain and in peripheral macrophages and lymphocytes. By influencing these pathways in the central nervous system, administration of aBC affects inflammatory neurological diseases, such as Alzheimer's Disease, Parkinson's Disease, amyotrophic lateral sclerosis and stroke.

Figure 2:
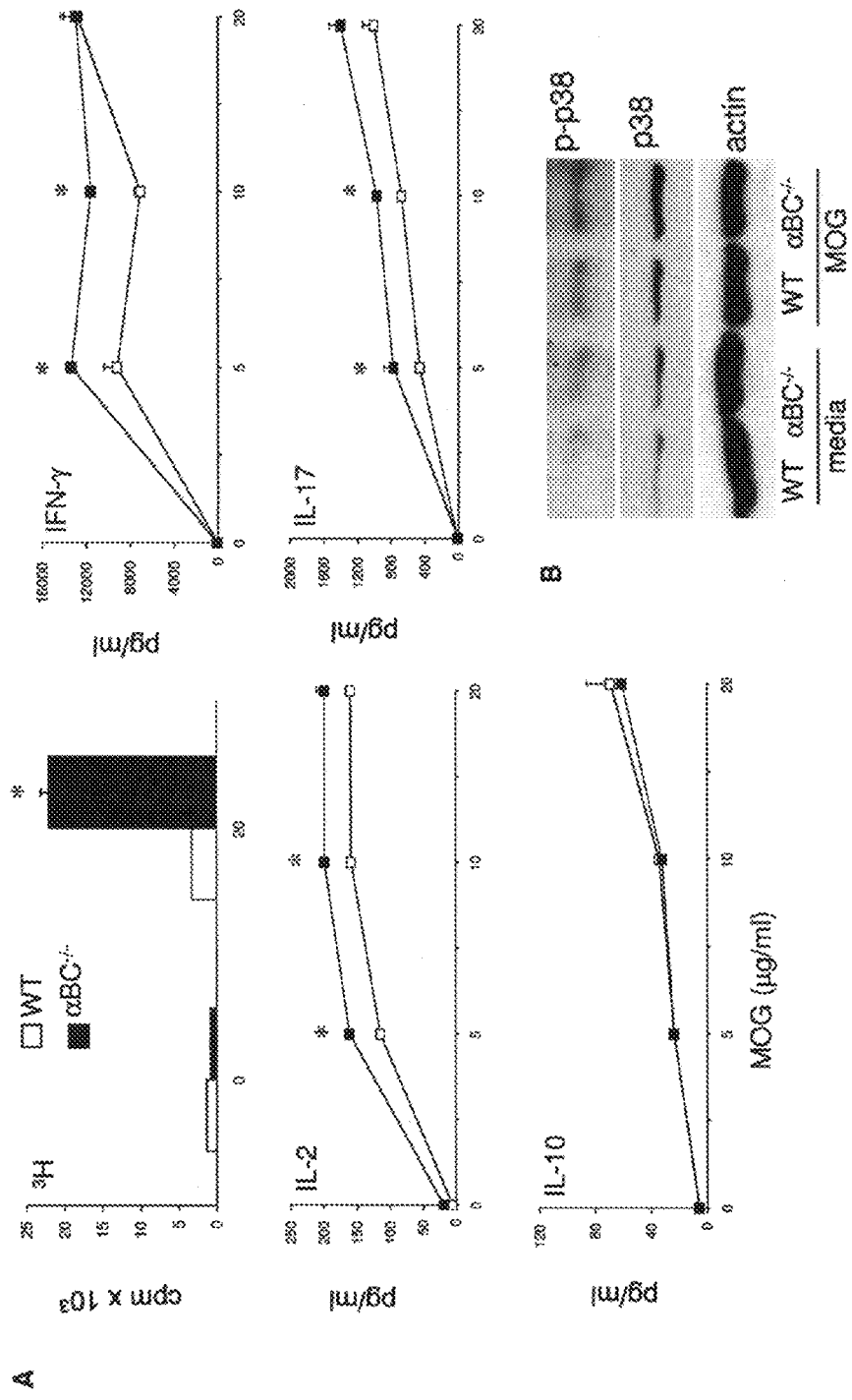
FIG. 2. T cells from $\alpha BC^{-/-}$ EAE mice are hyper-responsive. (A) Proliferation rate (cpm) and secretion of Th1 (IFN-γ, IL-2), Th17 (IL-17) and IL-10 cytokines (pg/ml) from CD3+ T cells isolated from WT (□) and $\alpha BC^{-/-}$ (■) EAE mice stimulated with syngeneic irradiated splenocytes and MOG 35-55 peptide. (B) Western blot of p-38 and phospho-p38 expression in CD3+ T cells from WT and $\alpha BC^{-/-}$ EAE mice stimulated with syngeneic irradiated splenocytes and MOG 35-55 peptide for 1 h.
Figure 4:
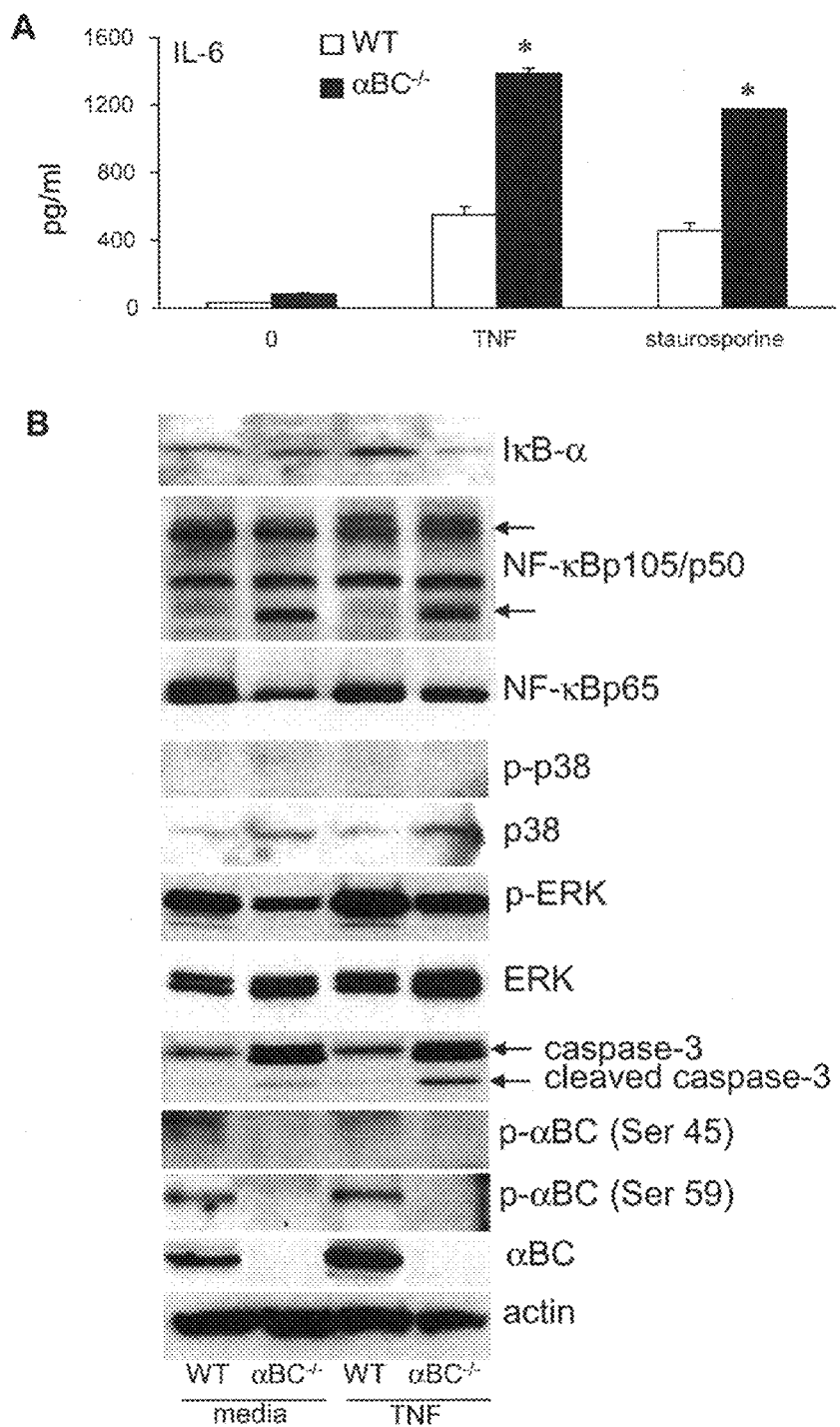
FIG. 4. $\alpha BC^{-/-}$ astrocytes are more susceptible to cell death and augment ERK and NF-κB signaling. (A) IL-6 production by WT (□) and $\alpha BC^{-/-}$ (■) astrocytes 48 h after TNF stimulation. (B and D) DNA binding activity of NF-κB p50 and NF-κB p65 in WT and $\alpha BC^{-/-}$ astrocytes 48 h post-TNF stimulation. (C) Expression of αBC, phospho-αBC, cleaved and uncleaved caspase-3, p-38, phospho-p-38, ERK, phospho-ERK, NF-κB p105/p50, NF-KB p65 and IκB-α molecules in WT and αBC null astrocytes 72 h after stimulation with TNF.
Figure 4:
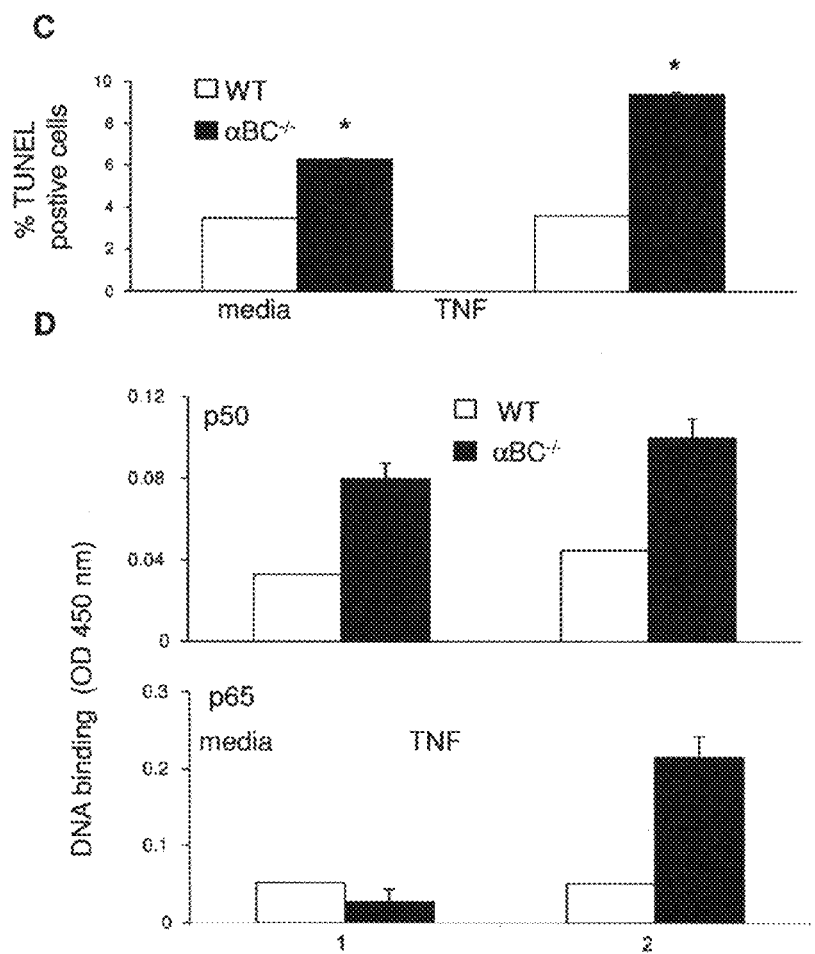

As shown in FIG. 1, administration of aBC reduces the production of pro-inflammatory cytokines in peripheral blood lymphocytes. As shown in FIG. 2, Absence of aBC reduces p38 mapK and ERK in peripheral T lymphocytes and macrophages FIG. 3, and in CNS astrocytes. Astrocytes deficient in aBC are defective in ERK signalling (FIG. 4).

In a number of disease conditions p38MapK and ERK play key roles. As shown in Table 1, the absence of aBC reduces inflammation, and administration reverses the effects of inflammation. In Table 2 we show that we reduce inflammation in brain by administering recombinant aBC. aBC also reduces the phosphorylation of p38MAPK and ERK, FIGS. 2B, 3B and 4B.

Administration of aBC is likely to diminish the extent and severity of ischemic lesions, including myocardial infarction, stroke and arterial occlusion.

Example 3

αB Crystallin Treats Established Autoimmune Arthritis in the Collagen-Induced Arthritis Model In addition to studies in the EAE model of MS, it is demonstrated herein that αBC treats established autoimmune arthritis in a rodent model of RA. In these studies mice were induced to develop collagen-induced arthritis with bovine type II collagen emulsified in complete Freund's adjuvant, and boosted 21 days later with bovine type II collagen in incomplete Freund's adjuvant.

After mice developed clinical arthritis, arthritic mice were randomized to receive every-other day treatment with αBC (10 µg every other day), myoglobin control protein (10 µg) or PBS (saline control). Mice with established arthritis treated with αBC demonstrated statistically reduced arthritis severity relative to mice treated with the myoglobin or PBS controls (P<0.05) (FIG. 11). Further, following sacrifice mouse joints were harvested, fixed, decalcified, paraffin-embedded, sectioned, stained with toluidine blue, and a binded examiner scored the sections for the degree of synovitis (inflammation), pannus (synovial lining growth) and destruction (bony erosions). Mice treated with αBC exhibited statistically reduced synovitis (p<0.05), pannus formation (p<0.05) and destruction (p<0.05) (FIG. 12). Additionally, splenocytes harvested from CIA mice treated with αBC exhibited reduced proliferative responses and proinflammatory cytokine (TNF and IFN-gamma) production (FIG. 13). Immunohistochemical analysis of RA synovium demonstrated high levels of aBC expression in RA pannus, while no significant expression was detected in the synovial lining derived from OA patients (FIG. 14).

Example 4

αBC Protects Hippocampal Neurons from Abeta-induced Apoptosis

Hippocampal tissue was harvested from E15-16 mouse pups and collected in ice cold calcium- and magnesium-free HBSS followed by trypsinization with 0.05% trypsin for 5 min at 37° C. Cells were dissociated and resuspended in serum-free DMEM/F12. Tissue culture wells (Costar 96-well A/2 plates, 0.16 cm$^2$/well) were precoated with 25 µL/well of poly-L-lysine (10 µg/mL in phosphate buffered saline; Sigma), for 1 h at 37° C. Following aspiration, each well received 45 pL of cell suspension (2000 neurons/well; 12,500 cells/cm2) and 5 µL of serum free DMEM/F12 medium containing N2 supplement and recombinant BDNF (R&D Systems Inc., Minneapolis, Minn.). Culture conditions including low cell density and serum-free DMEM were similar to those used for primary hippocampal cultures reported by Lindholm et al. (1996). 6-7 days in vitro (DIV) hippocampal neurons were exposed to culture medium alone (CM) or culture medium containing 4 µM Ab1-42 with or without 5-10 µM of recombinant human ±BC. After 72 hours, cultures were fixed and TUNEL assay performed. Cultures were photographed with fluorescence microscopy and DAPI and TUNEL-positive cells counted using Image Pro MDA 6.1. Data is expressed as mean±SE for n=20-40 fields counted in 1 experiment. The conditions were compared to Ab1-42 using ANOVA test (***p<0.001).

Example 5

Early Changes in Experimental Anterior Ischemic Optic Neuropathy and Treatment with αB Crystallin Anterior ischemic optic neuropathy (AION) is due to ischemia of the optic nerve head, leading to significant vision loss. Our goal was to study the early changes following optic nerve head ischemia and to test the efficacy of a potential therapy in experimental AION. We used a photochemical thrombosis model of AION in mouse, with laser-directed optic nerve head ischemia in the presence of rose bengal. Intracranial flash visual evoked potential (fVEP) recordings and histological methods were utilized. Within days after experimental AION, there was significant optic nerve head swelling, vascular leakage, loss of the peri-papillary microvasculature, and decrease in the amplitude of fVEP responses. Coincident with these changes, there was up-regulation of macro- and microglia. Interestingly, the expression of α-B crystallin (αBC), a small heat shock protein abundant in the lens of the eye, was significantly increased in the optic nerve head and retina at day one following experimental AION. This led us to test the effects of recombinant αBC in experimental AION. Short-term treatment of αBC did not dampen the post-ischemic responses in wild-type or in αBC knock-out mice and did not improved fVEP amplitude. In contrast, 3- week αBC treatment resulted in significantly improved fVEP latencies compared to placebo. αBC was acutely up-regulated in experimental AION. Short-term αBC treatment immediately following optic nerve head ischemia did not have significant effects, while a 3-week course of αBC injections led to a striking acceleration of visual pathway signal transmission, consistent with a mechanism of axonal protection.

AION is the most common acute optic neuropathy in patients over 50 years old, and the majority of patients suffer from permanent vision loss, with about 20% of patients at risk of contralateral involvement. Visual evoked potential recordings of patients with AION show different degrees of functional deterioration, including a decrease in the amplitude and a prolongation of the latency of responses. Non-arteritic AION is Presumed to result from ischemia of the optic nerve head, a watershed zone supplied by branches of the ophthalmic artery. Beyond that, the mechanism of disease is poorly understood, and there is currently no effective treatment.

Photochemical thrombosis animal models of AION have been instrumental in elucidating the events following optic nerve head ischemia.[6-10] In experimental AION, there is glial and axonal dysfunction, with optic nerve oligodendrocyte apoptosis occurring as early as day 6 and progressive nerve demyelination within the first 2 weeks after optic nerve head ischemia. Retinal ganglion cell loss occurs within 3 weeks following experimental AION, peaking during the first 2 and 3 weeks. Following experimental AION, there are important signs of self repair, such as the up-regulation of retinal heat shock proteins HSP 70, 84, and 86.

In this study, we used a mouse model of experimental AION to examine the early changes following optic nerve head ischemia. We then assessed the effectiveness of a small heat shock protein named α-B crystallin (αBC), using functional and histological approaches.

Methods

Animal Care and Sedation. All animal care and experiments were carried out in accordance with the ARVO guideline for the Use of Animals in Ophthalmic and Vision Research and the Stanford Administrative Panel on Laboratory Animal Care. Adult wild-type 129S2/Sv mice (Charles River, Taconic Farm) and αBC knockout mice, a gift of Eric Wawrousek (NEI), were used. All procedures were performed under sedation, achieved with ketamine 50-100 mg/kg, xylazine 2-5 mg/kg, and buprenorphine 0.05 mg/kg. When applicable, pupillary dilatation was performed using 1% tropicamide and 2.5% phenylephrine, following 0.5% proparacaine corneal anesthesia.

Optic Nerve Head Ischemia. Following sedation and pupillary dilatation, optic nerve head ischemia was achieved in the right eye of adult 129S2/Sv mice using laser-directed photochemical thromobosis. Immediately following rose bengal injection into the tail vein (1.25 mM in PBS, 2 µl per g body weight), we exposed the optic nerve head to 15-20 light spots of 200 ʄm diameter for 500 ms duration with a frequency doubled Nd:YAG laser (Pascal, OptiMedica).

Immunohistochemistry. Following intracardiac perfusion (India ink for angiogram or 4% paraformaldehyde in PBS for fixation), whole mount neuroretina was prepared following 3-4 radial cuts, post-fixed for 30 min, and mounted (Vectashield, Vector Labs, Burlingham, Calif.). For immunofluorescence microscopy, primary antibody with anti-Iba-1 rabbit polyclonal antibody (1:500-1000 dilutions, WAKO) or anti-GFAP monoclonal antibody (1:500-1000 dilutions, Sigma) and goat anti-rabbit or anti-mouse IgG secondary antibodies (1:200-400 dilutions, Invitrogen) were used. For paraffin-embedded or frozen horizontal sections, the eye and the entire optic nerve were dissected, treated per routine protocol, and 10 ʄm horizontal sections were prepared and H&E stained.

Western Blot. Protein was prepared from 3 pairs of eyes from adult mice one day post-AION per routine protocol in the presence of protease inhibitors. Protein concentrations were determined using micro BCA kit (Pierce). Equal amount of protein per lane was loaded onto a 10% mini-SDSPAGE gel (Invitrogen) and run per recommended protocol. Western blotting was carried out with anti-αBC rabbit polyclonal antibody (1:200 dilution, Abcam) and imaged per ECL protocol (Pierce).

Alpha-B Crystallin Treatment. Ten µg of recombinant human αBC (produced in E. coli, US Biological) diluted in sterile saline vs. saline alone was delivered under masked condition via the tail vein within 5 hrs of AION. For short-term treatment, the animals were injected once per day for 1-3 days. For long-term treatment, the animals (after 2 doses of short-term treatment) were injected every other day for 3 weeks (total 12 doses).

Electrode Implantation. Small burr holes were drilled in the skull overlying the binocular visual cortex on each side (2.5-3 cm lateral to the sagittal suture and 2-3 mm anterior to the lambdoid suture) for placement of small stainless steel screw electrodes (J. I. Morris, Southbridge, Mass.). Dental cement secured the electrodes over the skull, with several sutures to close the scalp. Implanted mice behaved like unimplanted mice, with normal response to stimuli, locomotion and weight gain over months.

Photopic fVEP Recording. While visual evoked potential reflects the function of the entire visual pathway, in this experimental setting we used serial flash visual evoked potential (fVEP) recordings to monitor optic nerve function. Every effort was taken to standardize the fVEP recordings, including the state and duration of sedation, body temperature (36.5-37.5° C.), circadian rhythm, and systemic hydration. Animals that developed permanent corneal or lens opacifications were rejected from the study. Pupils were undilated. A reference electrode was inserted near the nose, and a ground electrode, near the tail. Impedance was monitored before each trial. In the Ganzfeld dome (Diagnosys), implanted mice (4-5 months old) were exposed to white light flashes at 2 Hz (pulse duration≥4 ms) in background luminance of 20 cd sec/m2, which minimize light history variability. Data were acquired at 1 kHz and band pass filtered at 0.5-100 Hz. Each fVEP response trial was the average of 50 traces, with multiple trials recorded per luminance intensities (0.001 to 20 cd sec/m2) per day.

The animals recovered for one week following implantation, and baseline recordings included those with both eyes open and those with only the left or the right eye open. There were no VEP responses if both eyes were occluded. The recordings were under masked condition to eliminate bias. Since only a small number of animals could be recorded per day, the fVEP experiment with 3-week treatment was done twice, using aliquots from the same batch of αBC.

Data and Statistical Analysis. The amplitude and latency of $N_1$, the dominant fVEP waveform, were averaged from 30-50 trials (at least 3 trials from each mouse per time point) from 4-5 animals. Although data from up to 7 animals were available per group at some time points, only animals with data at every time point were included for data analysis for consistency. In response to very low-intensity visual stimuli (<1 cd sec/m$^2$), fVEP responses were not consistently obtained, thus data analysis was restricted to luminance intensities between 2.15 to 20 cd sec/m$^2$. The amplitude was calculated as the difference between the peak immediately before $N_1$, the dominant waveform, to the $N_1$ peak, which was defined by Espion. Amplitude range of 3-50 μV was used for analysis. The latency was calculated as the time to $N_1$ peak from stimulus onset, again calculated by Espion. Latency range of 30-80 ms was used, which included values of 3 standard deviations from the mean of the baseline data. Grubbs' test was used to check for outliers, which were rejected (0-3 per data point). While latencies for $N_1$ were extremely stable across several examinations in each mouse, their amplitudes showed more variability. The latency difference between the contra- and ipsilateral fVEP responses was about 2 ms. Data was analyzed with Excel and Origin, and statistical differences were determined using Student's t-test and one-way ANOVA.

Results

Experimental AION. We established a reliable mouse model of optic nerve head ischemia in our laboratory, achieved by photochemical thrombosis, with a frequency doubled Nd:YAG laser as a source of focused, low intensity light. Upon laser light exposure, the optic nerve head visibly whitened, consistent with ischemia. As reported previously,[6, 9] application of the laser to the optic nerve head in the absence of rose bengal did not cause optic nerve head ischemia. Intracardiac perfusion of India ink and retinal angiography in a whole mount preparation demonstrated swelling, leakage, and selective loss of the peri-papillary microvasculature, which supplied the mouse optic nerve head (FIG. 16A). Six weeks following experimental AION, H&E stained horizontal, paraffin-embedded sections confirmed ischemic changes at the optic nerve head, loss of retinal ganglion cells (FIG. 16B-C), and thinning of the optic nerve in the AION eyes (n=6 eyes each). Laser light exposure was also associated with the disruption of the retinal pigment epithelium and the presence of pigment-laden macrophages in the peri-papillary region (FIG. 16C and inset).

Early Changes and Up-Regulation of Alpha-B Crystallin. With this experimental AION model in hand, we focused on the. events most relevant to treatment considerations—those occurring within the first few days following optic nerve head ischemia. At day 3 following ischemia, there was increased Iba-1 expression at the optic nerve head of the laser light-exposed eyes (n=5 pairs of eyes) (FIG. 17). This microglial activation in the AION eyes was accompanied by an increased expression of glial fibrillary acidic protein (GFAP), a non-specific indicator of stress (n=5 pairs of eyes) (FIG. 17). These changes were limited to the peri-papillary region with microvascular loss and reminiscent of those found after laser-induced photochemical thrombosis in the retina and brain.

At day one following experimental AION, western blot analysis revealed a significant up-regulation of α-B crystallin (αBC), protein expression in the optic nerve head and neuroretina of the AION eyes compared to the control eyes (n=3 pairs of eyes) (FIG. 18). αBC is an important structural protein of the lens of the eye and a molecular chaperonin known to be induced in experimental glaucoma, retinal ischemia, and central nervous system diseases.

In contrast, comparing the AION and control eyes, there was no difference in the expression of class III β-tubulin, a major component of the neuronal microtubule which is highly expressed in the retinal ganglion cell body and axons.

We next determined if αBC is an important molecule in experimental AION by looking at mice lacking αBC which has been shown to be more sensitive to chemically induced retinal ischemia and oxidative stress. Whole mount neuroretina from the αBC knock-out mice demonstrated significantly elevated expression of Iba-1 and GFAP at the optic nerve head in the laser light-exposed eyes compared to the control eyes, similar to that in the wild-type mice (n=5 pairs of eyes). In H&E stained horizontal sections, there was qualitatively more prominent optic nerve head and optic nerve inflammation in the AION eyes 3 weeks following optic nerve head ischemia, compared to the control eyes (n=3 pairs of eyes each) (FIG. 19). There was also significant loss of retinal ganglion cells in the AION eyes as compared to the control eyes (FIG. 19C).

To determine if αBC is an effective therapy for AION, we treated mice in a masked fashion with intravenous recombinant αBC (10 μg per injection) vs. saline. Injections were initiated within 5 hrs of onset, then once per day, for a total of 3 days. Following 3 days of αBC treatment, there was an increase in Iba-1 expression in the laser light-exposed eyes, compared to the control eye, with no significant difference between the αBC-(n=7 pairs of eyes) vs. saline-treated groups (n=8 pairs of eyes). There was also elevated GFAP expression at the optic nerve head of the AION eyes, with no difference between the αBC-(n=5 pairs of eyes) vs. saline-treated (n=4 pairs of eyes) animals.

Since exogenous αBC may not have significant effects in a system that already has upregulated endogenous αBC, we looked for the effects of treating experimental AION in the αBC knock-out mice. Three-day αBC treatment of the αBC knock-out mice after AION induction did not affect the increase in Iba-1 and GFAP expression at the optic nerve head in whole mount neuroretina preparations (n=6 pairs of eyes per group), although there appeared to be decreased optic nerve head swelling in the αBC-treated, post-AION eyes.

We examined the functional effects of αBC treatment by recording serial flash visual evoked potentials (fVEP). To minimize variability, we implanted intracranial electrodes in the occipital lobes. Light stimulation of one eye led to prominent contralateral occipital cortical responses (FIG. 20A-B), consistent with the predominantly crossed rodent visual pathway. In the presence of increasing luminance intensities, $N_1$, the dominant fVEP waveform, exhibited increasing amplitudes and faster latencies (FIG. 20C). Overall, the latency was a highly consistent measurement, and there was greater variability in the amplitude data.

The fVEPs were recorded at baseline (pre-AION) and then at days 1-2 following experimental AION induction and initiation of daily 10 μg αBC vs. saline treatment (masked, first dose given within 5 hrs). At post-ischemic days 1-2, in response to flash stimuli at 20 cd sec/m², the αBC-treated group showed a 20.0% reduction in the amplitude (pre: 16.0±1.3 μV vs. days 1-2: 12.8±1.0 μV, p<0.05) and no significant change in the latency (pre: 53.6±1.2 ms vs. days 1-2: 52.1±1.3 ms, p>0.3) (FIG. 21B). At 20 cd sec/m2, the saline-treated group had a 19.3% reduction in the fVEP amplitude at days 1-2 (pre: 12.9±1.0 μV vs. days 1-2: 10.4±0.7 μV, p<0.05) and no significant change in latency (pre: 51.4±0.8 ms vs. days 1-2: 50.2±1.4 ms, p>0.7). Comparing αBC- and saline-treated groups at days 1-2, there was no significant benefit of short-term αBC treatment immediately following injury (amplitude p>0.05, latency p>0.3).

Three-Week αBC Treatment. We next looked at the effects of long-term αBC treatment. A 3-week injection regimen was chosen since significant retinal ganglion cell death occurs by this time. We injected αBC vs. saline every other day for 3 weeks and recorded weekly fVEP responses. In the αBC-treated group, there was no significant improvement of fVEP amplitude between days 1-2 and 3 weeks (days 1-2: 12.8±1.0 μV vs. day 21: 13.8±1.4 μV, p>0.5). In the saline-treated group, in contrast, there was a 55.1% improvement between days 1-2 and 3 weeks (days 1-2: 10.4±0.7 μV vs. day 21: 16.1±1.2 μV, p<0.0001) (FIG. 21B). Compared to baseline, there was no change in fVEP amplitude at day 21 in the αBC-treated group (p>0.2) but an improvement of 25.3% (p<0.05) in the saline-treated group. In response to brighter stimulus intensities, fVEP amplitude increased in a similar fashion between the αBC- and saline-treated groups at baseline and day 21 (FIG. 22A), with a greater variability of the amplitude data compared to latency (FIGS. 22 and 23).

At the 3-week endpoint, there was a dramatic improvement of fVEP latency in the αBC treated group but not in the saline-treated group (FIG. 21C). At day 21, in response to 20 cd sec/m²flash, fVEP latency was faster by 5.2 ms in the αBC-treated group compared to days 1-2 (days 1-2: 52.1±1.3 ms vs. day 21: 46.9±1.3 ms, p<0.03). Compared to baseline responses, this faster latency at day 21 was highly significant (p<0.0005), which was also evident across multiple luminance intensities between the 2 treatment groups (FIG. 22B). In the saline-treated group, there was no improvement between days 1-2 and day 21 at 20 cd sec/m2 (days 1-2: 50.2±1.4 ms vs. day 21: 50.5±0.9 ms, p>0.3), compared to baseline (51.4±0.8 ms, p>0.4), and across multiple luminance intensities (FIG. 22B).

We looked at the time course of fVEP latency improvement at weeks 1, 2, and 3 (FIG. 23). In the αBC-treated group, there was no improvement between days 1-2 and week 1 (days 1-2:52.1±1.3 ms vs. day 7: 50.3±1.3 ms, p>0.3). By week 2, however, there was already a significant latency improvement of 4.3 ms (days 13-15: 47.8±1.3 ms, p<0.02), which further improved to 5.2 ms by week 3 (p<0.03). This pattern was strikingly different from that of the saline-treated group, where there was no improvement at week 1 (days 1-2: 50.2±1.4 ms vs. day 7: 54.0±1.0 ms, >0.3), week 2 (days 13-15: 52.1±0.7 ms, p>0.9), or week 3 (day 21: 50.5±0.9 ms, p>0.3).

At the end of the 3-week treatment period, 5 pairs of eyes each from the αBC- and saline treated groups were cut into 10 μm frozen horizontal sections, H&E stained, and evaluated in a masked fashion. There was no significant difference in the number of retinal ganglion cell number in the αBC- vs. saline-treated groups, with a loss of retinal ganglion cells despite αBC treatment.

Within days of optic nerve head ischemia, there was micro- and macroglial activation at the optic nerve head and a concurrent decrease in optic nerve function. The up-regulation of αBC led us to test its ability to preserve visual function following experimental AION. Short-term αBC treatment did not have significant histological or functional effects, while long-term αBC treatment led to a dramatic improvement of fVEP latency at weeks 2 and 3. Taken together, our data suggested a protective effect of exogenous αBC on visual pathway signal transmission by improving optic nerve function following experimental AION.

Expressed in the retinal ganglion cells[30] and optic nerve glia,[24] αBC is poised to play a role in optic neuropathies. The up-regulation of αBC immediately following optic nerve head ischemia is consistent with its function as a small heat shock protein with both anti-apoptotic and neuroprotective actions.

The acceleration of fVEP responses following long-term αBC treatment was consistent with a mechanism of axonal protection. This improvement occurred during a period of known axonal loss and oligodendrocyte dysfunction in experimental AION. Curiously, the fVEP latency in the αBC-treated group improved beyond that of the baseline, which may be related to the direct effect of αBC on the optic nerve or from αBC-facilitated developmental acceleration. Here we provided functional evidence for the therapeutic value of this treatment.

Example 6

Therapeutic Role of αB-crystallin, an Endogenous Neuroprotectant, in Stroke

Stroke is the most common cause of disability and the third most common cause of death in adults worldwide. The only US Food and Drug Administration (FDA) approved treatment is tissue plasminogen activator (tPA), where therapy is time dependent and must be given within 4.5 hours of stroke onset. Consequently, there is an unmet need, for therapy that could be administered later than tPA and is directed to protection rather than clot dissolution. Described herein is an effective treatment of stroke, even 12 h after onset, by the administration of alphaB-crystallin (Cryab), an endogenous immunomodulatory neuroprotectant. In Cryab⁻/⁻ mice, there was increased lesion size and diminished neurologic function after stroke compared to wild-type mice. Increased plasma Cryab was detected after experimental stroke in mice and after stroke in human patients. Administration of Cryab even 12 hours post-experimental stroke provided clinical benefit and reduced stroke pathology. Inflammatory cytokines associated with stroke pathology were reduced with exogenous administration. Cryab is an endogenous anti-inflammatory and neuroprotectant molecule produced after stroke, whose beneficial properties can be augmented when, administered therapeutically at an unprecedented time after stroke.

There are several molecular mechanisms involved in the progression and evolution of the damage caused by stroke including oxidative/nitrosative stress, excitotoxicity, apoptosis, calcium dysregulation, and inflammation. Although several therapeutic approaches have been shown to be effective in various stroke animal models, the only FDA-approved drug is tPA which acts through conversion of plasminogen into active plasmin to cleave the blood clot. tPA exemplifies strategies that aim to alter the obstructive blood clot, rather than protect the damaged brain.

Cryab, a member of the family of small heat shock proteins, designated sHSP B5, is constitutively expressed in the lens of the eye and muscle and is induced in many types of brain injury. Cryab is the most abundant induced transcript in multiple sclerosis (MS) lesions, and is highly expressed in areas of inflammation. Cryab has both anti-apoptotic and immunomodulatory properties. When first described in MS lesions, it was described as an auto-antigen, however subsequent studies demonstrated that Cryab acted as a negative regulator on inflammation and that it was imbued with protective properties for the nervous system.

To investigate the effects of Cryab deficiency on cerebral ischemia, wild-type and Cryab$^{-/-}$ mice were exposed to 30 minutes of middle cerebral artery occlusion. The Cryab$^{-/-}$ mice had significantly larger lesion sizes at 2 days (2 d) as assessed by triphenyltetrazolium chloride (TTC) staining. This difference remained at 7 days (7 d) after stroke as assessed by silver stain, indicating that the deficiency of Cryab affected both the early and delayed phases of ischemic damage. Functional outcome was assessed by a 28-point neurological scoring test. The Cryab$^{-/-}$ mice had significantly worse scores at both 2d and 7d time points compared to wild-type controls. No differences were seen in cerebral blood flow measured by laser doppler flow-meter immediately after the occlusion and at 15 and 30 minutes of reperfusion between the groups.

We analyzed levels of Cryab in plasma in wild-type mice before and at 12 h, 2 d and 7 d after stroke onset by ELISA. The Cryab levels were significantly increased at the 12 h time point with a gradual decrease over the ensuing seven days time period. We also examined the plasma concentrations of Cryab in patients with ischemic stroke who were admitted to Stanford Stroke Center and healthy young individuals. The patients were grouped according to their age, as younger (age between 39 and 66) and older (age between 82 and 93). All patients were treated according to Stanford Stroke Center's current protocols. The Cryab levels at presentation to the hospital (less than 4 h after symptom onset for all patients) were higher in the younger patient population compared to the control group. However, the older patients did not show increased levels of Cryab. Because the lesion size might affect the response, the lesion volumes were determined by diffusion-weighted magnetic resonance imaging. Although the mean lesion volume was higher in the older population, there was no significant difference between older and younger patient groups. Interestingly, the lesion volume and the plasma Cryab levels at presentation highly correlated only in the younger patient group and not in the older group, perhaps indicating that the body's endogenous response to stroke is age-dependent. These findings have not been observed before for any small heat shock protein after stroke.

To test the hypothesis that increased plasma Cryab after stroke was beneficial, Cryab$^{-/-}$ mice were given intraperitoneal injections of recombinant Cryab protein starting 1 h before stroke onset and continuing at 12 h, 24 h and daily afterwards for seven days in total. The lesion sizes in the Cryab treated Cryab$^{-/-}$ mice were significantly decreased, to the levels of PBS treated wild-type mice, compared to PBS treated Cryab$^{-/-}$ mice.

The effects of Cryab treatment on splenocytes isolated from PBS treated wild-type and Cryab$^{-/-}$ mice and Cryab treated Cryab$^{-/-}$ mice were assessed at 7 d after stroke. Splenocytes from PBS treated Cryab$^{-/-}$ mice produced more pro-inflammatory IL-2, IL-17 and TNF when stimulated with anti-CD3/anti-CD28 than both PBS-treated wild-type mice and Cryab-treated Cryab$^{-/-}$ mice splenocytes. When stimulated by concanavalin-A, splenocytes from PBS treated Cryab$^{-/-}$ mice produced more pro-inflammatory IFN-γ, TNF, IL-12p40 and less anti-inflammatory IL-10 compared to the splenocytes from both PBS treated wild-type and Cryab treated Cryab$^{-/-}$ mice. When stimulated with LPS, splenocytes from PBS treated Cryab$^{-/-}$ mice produced more TNF and less IL-10 compared to the splenocytes from both PBS treated wild-type mice and Cryab treated Cryab$^{-/-}$ mice. These data indicate that restoration of plasma Cryab by systemic treatment modulates the peripheral inflammatory response and is sufficient to decrease the lesion sizes in Cryab$^{-/-}$ mice to the levels of wild-type mice after stroke.

Because the restoration of plasma Cryab in Cryab$^{-/-}$ mice decreased the lesion size, we next investigated whether administration of Cryab into wild-type mice would have a similar effect. When Cryab was administered 1 h before and 12 h after the stroke onset, the lesion size at 2 d was not different between PBS and Cryab treated wild-type mice groups. However, when it was administered 1 h before, 12 h and 24 h after and daily afterwards for seven days in total, the lesion sizes were significantly reduced in Cryab treated group compared to the PBS treated group. Moreover, even starting the initial treatment 12 h after the stroke onset, making the treatment highly relevant if translated into the clinic, conferred neuroprotection in the Cryab-treated group.

To investigate the role of the immune system in ischemic neuropathology associated with stroke, the profile of mononuclear cells in the ischemic wild-type and Cryab$^{-/-}$ brains was characterized. We identified four distinct cell populations according to their CD45 and CD11 b expression patterns: CD11b$^+$CD45$^{low}$ (microglia), CD11 b$^{high}$CD45$^{high}$ (granulocytes and macrophages), CD11b$^{low}$CD45$^{high}$ (subpopulation of monocytes), CD11b$^{negative}$CD45$^{high}$ (lymphoid cells). The brain invasion of granulocytes and macrophages was higher in both groups at the earlier (2 d) time point whereas the lymphoid cells increased more at the later (7 d) time points, consistent with other reports. The total number of microglial cells was equivalent in wild-type and Cryab$^{-/-}$ mice at both the 2 d and 7 d time points. However, the numbers of granulocyte and macrophage populations and the subpopulation of monocytes were significantly higher in the Cryab$^{-/-}$ mice brains at 2 d but not at 7 d compared to wild-type mice. Moreover, the numbers of lymphoid cells were significantly higher in the Cryab$^{-/-}$ group at 7 d.

The granulocyte and macrophage population was further analyzed with Gr1 and F4/80 markers to identify granulocytes and macrophages separately. In the CD11b$^{high}$CD45$^{high}$ population, three subpopulations were identified: F4/80$^{negative}$Gr1$^{positive}$ (granulocytes), F4/80$^{positive}$Gr1$^{positive}$ (activated macrophages), F4/80$^{positive}$Gr1$^{negative}$ (macrophages). There were More granulocytes and significantly higher numbers of activated macrophages in Cryab$^{-/-}$ mice at 2 d. The number of macrophages was equivalent at both time points between the groups.

The analysis of T cells (CD3$^+$) showed that the total number of T cells increased at 7 d compared to 2 d in both groups and there were significantly more T cells in the brains of Cryab$^{-/-}$ mice than wild-type mice at 7 d. When we analyzed the T cell subpopulations, no difference in CD4$^+$ and CD8$^+$ T cells were observed between wild-type and Cryab$^{-/-}$ groups. However, there were significantly more γδ-TCR$^+$ (γδ-T) cells in the brains of Cryab$^{-/-}$ mice at 2 d and 7 d after ischemia.

The number of all cell populations in spleens of Cryab$^{-/-}$ mice was significantly decreased at 2 d after stroke, suggesting a stronger inflammatory response associated with larger lesion sizes. There was no difference in the numbers of splenocyte populations before and 7 d after stroke between wild-type and Cryab$^{-/-}$ mice. There were no differences in the number of CD11b$^{+}$ cells and CD3$^{+}$, CD4$^{+}$ and CD8$^{+}$ T cells in blood of wild-type and Cryab$^{-/-}$ mice before, 2 d and 7 d after stroke. However, there were more γδ-T cells in blood of Cryab$^{-/-}$ mice before and 7 d after, but not 2 d after stroke. The difference of blood γδ-T cell numbers between Cryab$^{-/-}$ and wild-type mice was 2.7-fold before stroke whereas it was 6-fold at 7 d, implying a stronger inflammatory response in Cryab$^{-/-}$ mice. There were no differences in the number of any mononuclear cell Populations in the brains of wild-type and Cryab$^{-/-}$ mice before stroke.

Cryab has been shown to have both anti-inflammatory properties by inhibition of NF-κB and p38 MAP kinase as well as anti-apoptotic properties by inhibition of activation of caspase-3. To dissect whether the more vigorous inflammatory response seen in Cryab$^{-/-}$ mice might be due to the larger lesion sizes in Cryab$^{-/-}$ mice, or vice versa, we performed bone marrow chimera experiments. After a lethal dose of total body gamma irradiation, wild-type or Cryab$^{-/-}$ bone-marrow cells were injected into either wild-type or Cryab$^{-/-}$ mice to regenerate the immune system. We had four groups: wild-type cells transferred to wild-type hosts (WT→WT), wild-type cells transferred to Cryab hosts (WT→KO), Cryab$^{-/-}$ cells transferred to wild-type hosts (KO→WT), and Cryab$^{-/-}$ cells transferred to Cryab -/- hosts (KO→KO). The irradiation was established to be lethal by the death within two weeks of irradiated wild-type and Cryab$^{-/-}$ mice that were not given the cells. Six weeks after the irradiation, we confirmed the chimerism by PCR of blood leukocytes for Cryab so that the mice that were given wild-type and Cryab$^{-/-}$ cells had only wild-type and Cryab$^{-/-}$ genotypes in their immune system, respectively. The KO→KO group had significantly larger lesion sizes than WT→WT group. This is concordant with the previous finding of Cryab$^{-/-}$ mice having larger lesions than wild-type mice. The KO→WT group had significantly larger lesions than WT→WT group. There was also a trend of larger lesions in KO→KO group than WT→KO group. Taken together these studies all indicate that a deficiency of Cryab in the immune system is associated with larger lesions in both wild-type and Cryab$^{-/-}$ hosts. Therefore, the presence or absence of Cryab in the immune system is critical in the evolution of infarct. Furthermore, WT→KO group had significantly larger lesions than WT→WT group. There was also a trend of larger lesions in KO→KO group than KO→WT group. This suggests that the difference in lesion sizes between wild-type and Cryab$^{-/-}$ mice is not only due to the Cryab deficiency in the immune system but also due to the deficiency of Cryab outside the immune system, and within the central nervous system, as well. These results indicate that Cryab deficiency in both the immune system and as well as Cryab deficiency in brain each independently contribute to the larger lesions in Cryab$^{-/-}$ mice compared to wild-type mice.

Our findings describe a therapeutic role for Cryab in stroke, and emphasize how it functions as an endogenous neuroprotectant in stroke. Administration of Cryab augments a naturally occurring anti-inflammatory pathway.

Methods

Mice. All the animal procedures were approved by Stanford University Administrative Panel on Laboratory Animal Care. Cryab$^{-/-}$ mice were first generated with a 129S4/SvJae background and maintained in 129S6/SvEvTac X 12954/SvJae background. They are fertile and viable with normal lens transparency and without any apparent prenatal defects. At around 40 weeks of age they start to show postural defects and progressive myopathy. Since we studied younger mice (12-14-week-old), we do not anticipate any possible effects of myopathy in our study. The Cryab$^{-/-}$ mice have also a deletion of Hspb2. However, since it is not normally expressed in brain and in any lymphoid cell, it is unlikely that it would have any effects on the neurobiological and immunological processes involved in this study. Additionally, unlike Cryab, Hspb2 is not heat-shock inducible so it is unlikely for it to act as a general chaperone. Therefore, the effects observed in this study can be attributed to Cryab deficiency only, and not Hspb2 deficiency. The Cryab$^{-/-}$ mice were maintained and bred in our animal colony. Age matched, male 129S6/SvEvTac mice (Taconic Farms) were used as the wild-type controls.

Induction of cerebral ischemia. We used 12 to 14-week-old, male mice weighing 25-30 g. The weights of the animals in all experimental groups were similar. We used filament occlusion model of cerebral ischemia as described. Briefly, mice were anesthetized with 2% isoflurane in a mixture of 20% oxygen and 80% air. After the surgical exposure, the left external and common carotid arteries were permanently ligated. Then, a 7-0, silicon rubber-coated, reusable monofilament (Doccol Inc, 70SPRe2045) was inserted into the left common carotid artery and advanced towards the left internal carotid artery 9-10 mm after the left carotid bifurcation. The core body temperature was checked by a rectal probe and maintained at 37° C. throughout the surgery by a heating pad and lamp. The cerebral blood flow was measured by a laser Doppler flow-meter and at least 80% reduction compared to presurgical baseline values was achieved after the insertion of the filament. The flowmeter probe was placed 2mm posterior and 5-6 mm lateral to the bregma on the skull. The reperfusion was achieved by withdrawal of the filament 30 min after the insertion. After the closure of the surgical wound and the mice were returned to their cages with free access to water and food.

Assessment of lesion size. On day 2 after ischemia, the mice were sacrificed by deep anesthesia. 2mm thick, coronal sections of brains were stained with 2% triphenyltetrazolium chloride (TTC) for lesion size determination. On day 7 after ischemia, the mice were perfused transcardially by 30ml of 0.9% sodium chloride solution followed by cold 3% balanced formalin solution. The brains were incubated overnight in the 3% formalin solution and then transferred into 20% sucrose-3% formalin solution until they sank. Then, 30 μm thick sections were cut by using a cryostat. 1 in every 16 sections (11 sections per brain) were stained by the high-contrast silver stain method, scanned at 1200 dpi. The total ipsilateral, contralateral and the infarct areas were measured by using ImageJ (NIH). The lesion size was determined by this formula: the lesion size=100×[total contralateral hemisphere area−(total ipsilateral hemisphere area−infarct area)]/(total contralateral hemisphere area).

Flow cytometry analysis. After blocking the cells with 1% anti-mouse CD16/32 (eBioscience) antibody and 10% mouse serum (Jackson ImmunoLab) in MRB buffer (5% bovine serum albumin (Sigma) and 2 mM EDTA in PBS), the cells were stained with anti-mouse CD45 (30-F11), CD11b (M1/70), Gr1 (RB6-8C5), F4/80 (BM8), CD3 (17A2), CD8b (eBioH35-17.2), γδ-TCR (UC7-13D5) (eBioScience) and CD4 (RM4-5), Live/Dead Aqua (Invitrogen). We performed the flow cytometry on a Becton Dickinson LSR-II (Stanford Shared FACS Facility) and analyzed the data by FlowJo (TreeStar Inc). Gates were set accordingly and the compensation was done by single-color stained BD-CompBeads (BD Biosciences).

Human subjects and sample collection. Patients who presented to the emergency department with acute ischemic stroke were prospectively enrolled. Plasma samples were collected at presentation as well as 24 and 72 +/−8 hours after presentation. All patients underwent a detailed clinical history including stroke risk factors, physical exam, National Institutes of Health Stroke Scale (NIHSS) and basic laboratory testing. All patients initially had computer tomography imaging to rule out intracranial hemorrhage and then went on to obtain magnetic resonance imaging with diffusion-weighted imaging. If patients were within the time window for intravenous tPA or catheter based procedures they were treated accordingly. The healthy individuals (ages between 23 and 33, 2 females and 3 males) without any chronic medical condition were included into the study and used as healthy control group. Blood drawn was stored in EDTA tubes, placed on ice for transport and processed within 1 hour of venipuncture. The tubes were centrifuged at 3500 g for 5 minutes at 4° C. The plasma fraction was then separated and aliquoted into separate tubes stored at −80° C. prior to processing.

Measurement of Cryab in mouse and human plasma. 1 ml mouse blood was collected in syringes containing 50 µl 0.5M EDTA via cardiac puncture, placed on ice, centrifuged at 3000 g for 10 minutes at 4° C. The plasma fraction was collected and stored in separate tubes at −80° C. until further processing. The plasma levels of Cryab were assessed in duplicates by using a Cryab-specific ELISA kit (Stressgen Inc) according to manufacturer's protocol.

Bone marrow-chimeric mice. 8-week-old, male SV129 wild-type and Cryab$^{-/-}$ recipient mice underwent a lethal dose of 1000 cGy total body gamma irradiation in two split doses given with a 3 h interval. Within 3 h after the second dose, $5.5 \times 10^6$ bone marrow cells from 6-week-old, male wild-type and Cryab$^{-/-}$ mice were injected intravenously. 3 wild-type and 3 Cryab$^{-/-}$ mice were not given the cells and they all died within two weeks after the irradiation, confirming that the irradiation was lethal without the reconstitution of the bone marrow. 6 weeks later, appropriate reconstitution was confirmed by PCR of blood leukocytes.

Statistical analysis. All values were expressed as mean±s.e.m. For lesion size and neuroscore test, we performed two-tailed Student's t test for comparison of two groups and analysis of variance followed by post hoc Tukey test for multiple comparisons, respectively, after confirming the normal distribution of the datasets by Kolmogorov-Smirnov test. The non-parametric data were analyzed by Mann-Whitney U test for comparison of two groups and Kruskal-Wallis test with post hoc Dunn test for multiple group comparisons. We used GraphPad Instat 3.05 (GraphPad Software Inc). P values<0.05 were considered statistically significant.

Neurological score assessment. The neurological scores were assessed by a 28-point neuroscore test by an experimenter blinded to the experimental groups at 12 h, 2 d and 7 d. The mice were evaluated in seven categories and scored from 0 to 4 in each category. These categories were body symmetry (0: normal, 1: slight asymmetry, 2: moderate asymmetry, 3: prominent asymmetry, 4: extreme asymmetry), gait (0: normal, 1: stiff, inflexible, 2:limping, 3: trembling, drifting, falling, 4: does not walk), climbing at 45 angle (0: normal, 1: climbs with strain, limb weakness present, 2: holds onto slope, does not slip or climb, 3: slides down slope, unsuccessful effort to prevent fall, 4: slides immediately, no efforts to prevent fall), circling behavior (0: not present, 1: predominantly one sided turns, 2: circles to one side, not constantly, 3: circles constantly to one side, 4: pivoting, swaying or no movement), front limb symmetry (suspended by tail) (0: normal, 1: light asymmetry, 2: marked asymmetry, 3: prominent asymmetry, 4:slight asymmetry, no body/limb movement), compulsory circling (front limbs on bench, rear suspended by tail) (0: not present, 1: tendency to turn to one side, 2: circles to one side, 3: pivots to one side sluggishly, 4: does not advance), whisker response (0: symmetrical response, 1: light asymmetry, 2: prominent asymmetry, 3: absent response contralaterally, diminished ipsilaterally, 4: absent proprioceptive response bilaterally).

Isolation of immune cells from brain, spleen and blood. After removal of the blood into heparinized syringes and removal of the spleen, the mice were perfused transcardially with 30 ml cold saline and the brains were removed immediately. We split the hemispheres and homogenized the tissue by passing through a 70 µm cell strainer in HBSS (Gibco). Then, the homogenates were incubated in 1 ml of 2U/ml of Liberase CI (Roche) in HBSS for one hour at 37° C. and followed by 30% Percoll centrifugation. The cells were collected as the pellet and washed with 10% FBS in DMEM (Gibco). The spleens were passed through a wire mesh and the red blood cells (RBC) were lysed by lysis buffer (7.47 g ammonium chloride and 2.04 g tris base in 1L ddH2O, pH:7.6) and then the cells were washed with 10% DMEM-FBS solution. After the lysis of RBCs by lysis buffer the cells obtained from the blood were washed with 10% FBS in DMEM and kept on ice until staining.

Measurement of lesion volume in stroke patients. MRI lesions were analyzed using Medical Image Processing Analysis and Visualization (MIPAV) software. Restricted diffusion lesions were qualitatively identified by a hyperintense signal on B1000 and a corresponding hypointense signal on ADC map. Acute lesions were outlined on DWI to measure absolute stroke volumes. Typical imaging parameters were B=0, 1000 sec/mm$^2$; TR/TE=6000/73.2 ms; FOV=240 mm; slice thickness/gap=5/1.5 mm. TR, repetition time; TE, echo time; FOV, field of view.

Cloning, expression, purification and administration of T7-human Cryab. The full length clones of human Cryab was obtained from Open Biosystems. The proteins were cloned by introducing an EcoR1, an ATG site, a HindIII, and stop site using PCR. The resulting Cryab PCR fragment was ligated into the EcoR1-HindIII restriction site of pET21b (+) (Novagen) in frame with the amino terminal T7-tag. One-shot TOP10 cells (Invitrogen) were transformed with the resulting plasmid. Several of the resulting colonies were selected, expanded, and the insertion was verified by restriction digest with EcoR1 and HindIII, and sequencing. The protein was produced in small scale by transforming BL21 Codon Plus cells (Stratagene) for protein expression. A total of seven clones were selected from three different plates and were separately inoculated into 1 ml of LB broth containing chloramphenicol and carbenicillin overnight. An aliquot (50 µl) transferred to 1 ml of LB broth containing carbenicillin, incubated hours, induced with IPTG, and incubated another two hours. The population was assayed by mixing 20 µl of culture with 20 µl with SDS gel loading buffer and the samples were separated on a 10%-20% acylamide minigel.

Larger scale production and purification of T7-Cryab was accomplished by growing selected colonies in 250-1000 ml of LB broth with carbenicillin, induced with IPTG, and isolating the bacteria 4-12 hours later. The cells were lysed with a bacterial protein extraction buffer (Thermo) with sonication while being cooled on ice, and the supernatant collected after centrifugation, saturated ammonium sulfate was added to 20% v/v, and the mixture centrifuged. Sufficient saturated ammonium sulfate was added to the supernatant to increase the concentration of the solution to 50% v/v. After centrifugation the pellet containing Cryab was resuspended in 0.1M Tris pH 8.0 and applied to an anti-T7 column, and the T7-Cryab eluted with glycine buffer pH3.0. The eluate was neutralized with 1M Tris pH 8.0, concentrated, and applied to a Sephacryl S-300 column. The fractions corresponding to the large Mr sHsp (approx. 400 kD) were pooled and concentrated. The purity of the protein was established using Coomasie stained SDS PAGE gels, while the structure was confirmed by mass spectrometry. The quaternary structure was established using gel filtration on Sephacryl S-300 and by dynamic light scattering.

Peripheral immune cell activation and cytokine analysis. Splenocytes were isolated from PBS treated wild-type and Cryab-/- mice and Cryab-treated Cryab-/- mice one week post-stroke and cultured in flat bottomed, 96-well plates in media (RPMI 1640 supplemented with 2mL L-glutamine, 1 mM sodium pyruvate, 0.1 mM non-essential amino acids, 100 U/mL penicillin, 0.1 mg/mL streptomycin, 0.5 μM 2-mercaptoethanol, and 10% fetal calf serum). Cells were stimulated with LPS (100 ng/mL and 1 μg/mL), Concanavalin A (2μg/mL), or plate-bound anti-CD3 (5 μg/mL) and anti-CD28 (10 μg/mL). For all activation assays, splenocytes were pooled from three mice per group and triplicate wells were plated. Supernatants of cells were collected at the time of peak production for each cytokine (48 hrs: IL-2, IL-12p40; 72 hrs: TNF and IFN∀; 96 hrs: IL-17; 120 hrs: IL-10). Cytokines were measured in the supernatants using anti-mouse OPTEIA ELISA kits (BD Pharmingen for IFNα, IL-10, IL-2 and IL-12p40; R&D Systems for IL-17 and TNF).

Example 7

Exogenous αB-crystallin (CryAB) Improves Myocardial Function and Attenuates Apoptosis in Ischemia-reperfusion (I/R) Injury we investigateD the protective effect of exogenous CryAB administration on murine cardiac function after myocardial I/R injury in vivo and establishED an anti-apoptotic role in endothelial cells in vitro.
Results LVEF increases 1.8-fold after CryAB administration as determined by MRI. C57BL/6 mice underwent 30 minutes of I/R injury with pre-reperfusion IM injection of either PBS (N=6) or CryAB 50 mcg (N=6) 15 minutes prior to reperfusion. Animals were treated QOD with 50 mcg of CryAB by IP injection. On POD 40, there was a significant 1.8-fold increase in LVEF in CryAB-treated compared to PBS-treated animals (27±6% vs. 15±4%, p<0.005).

CryAB-treated hearts have decreased fibrosis on POD 40. On POD 40, hearts were recovered and processed to detect overall fibrosis. Animals treated with CryAB showed decreased Masson's trichrome staining in their myocardial tissue versus untreated animals.

CryAB-treated hypoxic HMEC-1 cell lines have decreased apoptosis in vitro. In order to investigate the potential mechanism behind the improvement in cardiac function, three assays were employed to assess the effect of CryAB on apoptosis in vitro on endothelial cells—the initiation site of I/R injury. First, HMEC-1 cultures were treated with CryAB 50 mcg during 6, 12, and 24 hours of hypoxia (1% $O_2$, 5% $CO_2$, 94% $N_2$). After each respective time point, cells were collected and western blot analysis revealed an overall trend towards decreased free bax, cleaved caspase-3, cleaved caspase-9, cleaved-PARP; and increased total Bcl-2 protein levels when cells were treated with CryAB compared to untreated hypoxic cells (FIG. 2a).

To assess overall cell death through an apoptotic pathway, an ELISA to detect cytoplasmic histone-associated DNA fragments was undertaken on HMEC-1 cultures after 24 hours of hypoxia (1% $O_2$, 4% CO2, 95% $N_2$). CryAB-treated (50 mcg) HMEC-1 cells had a significant 1.5-fold decrease in cytoplasmic histone-associated DNA fragments versus untreated hypoxic HMEC-1 cells (0.1475±0.0187 vs. 0.0972±0.0231, p<0.01).

Lastly, caspase-3 activity was evaluated for both CryAB-treated (50 mcg) and untreated 24 hour hypoxic HMEC-1 cells. CryAB-treated HMEC-1 cultures had a significant 2.7-fold decrease in caspase-3 activity versus untreated hypoxic cells (27.4286±7.6019 vs. 10.4177±2.1862, p<0.005).

This is the first study to investigate the role of exogenous CryAB on cardiac function after I/R injury in vivo using MRI. Our study demonstrates significant improvement in overall LVEF by almost twofold after 30 minutes of I/R injury, as well as, the administration of CryAB 15 min prior to reperfusion (providing a protective effect) into C57BL/6 WT mice.

Once it was known that exogenous CryAB significantly improved cardiac function, we sought to determine a mechanism behind this positive effect. Our results clearly demonstrate for the first time that vascular endothelial cells, in particular HMEC-1 cells, subjected to 24 hours of hypoxia-induced stress while incubated alongside with exogenously administered CryAB reduces overall apoptotic cell death as well as caspase-3 activity.

Upon endothelial cell injury through hypoxia in vitro or UR injury in vivo, extracellular CryAB (whether recombinant or through cellular release) may act to decrease overall endothelial cell apoptosis through a variety of pathways most notably the Bcl-2/caspase-3,9 pathway, and therefore prevents further cardiac vessel death and subsequent cardiomyocyte damage.

In conclusion, exogenous administration of CryAB to C57BL/6 WT mice significantly improves overall LVEF compared to untreated age-matched WT mice after I/R injury in vivo. CryAB-treated HMEC-1 cells exhibit decreased apoptosis in vitro in response to hypoxic stress. The improvement in cardiac LVEF may be due to the anti-apoptotic effects of CryAB.

What is claimed is:

1. A method for inhibiting neuromyelitis optica in a patient, the method comprising:
   administering to said patient a therapeutically effective dose of alpha B-crystallin protein.
2. The method of claim 1, wherein the agent is administered systemically.
3. The method of claim 2, wherein a route of systemic administration is selected from the group consisting of intraperitoneal, intravenous, intramuscular and subcutaneous administration.
4. The method of claim 3, wherein administration is intravenous.
5. The method of claim 1, wherein the patient is diagnosed as having neuromyelitis optica prior to the administering step.
6. The method of claim 1, further comprising:
   monitoring the activation of T cells in tissues affected by neuromyelitis optica.
7. The method according to claim 1, wherein said agent is a fusion polypeptide of αBC and an immunoglobulin Fc polypeptide.

* * * * *